US012605710B2

(12) United States Patent
Akita et al.

(10) Patent No.: US 12,605,710 B2
(45) Date of Patent: Apr. 21, 2026

(54) FLOW CHANNEL STRUCTURE FOR REMOVING FOREIGN SUBSTANCE, METHOD FOR REMOVING FOREIGN SUBSTANCE, AND METHOD FOR MANUFACTURING LIPID PARTICLES

(71) Applicant: KABUSHIKI KAISHA TOSHIBA, Tokyo (JP)

(72) Inventors: Masato Akita, Kawasaki (JP); Arisa Fukui, Yokohama (JP); Mitsuko Ishihara, Setagaya (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 320 days.

(21) Appl. No.: 18/182,638

(22) Filed: Mar. 13, 2023

(65) Prior Publication Data

US 2023/0219090 A1 Jul. 13, 2023

Related U.S. Application Data

(63) Continuation of application No. PCT/JP2022/009434, filed on Mar. 4, 2022.

(30) Foreign Application Priority Data

May 31, 2021 (JP) ................................ 2021-091332

(51) Int. Cl.
*B01L 3/00* (2006.01)
*A61K 9/16* (2006.01)
(Continued)

(52) U.S. Cl.
CPC ...... *B01L 3/502761* (2013.01); *A61K 9/1617* (2013.01); *A61K 9/1682* (2013.01);
(Continued)

(58) Field of Classification Search
None
See application file for complete search history.

(56) References Cited

U.S. PATENT DOCUMENTS

2008/0023324 A1* 1/2008 Ban .................. B01L 3/502753 422/68.1
2015/0125947 A1* 5/2015 Korczyk ............ F16K 99/0017 422/502
(Continued)

FOREIGN PATENT DOCUMENTS

CN 111485016 A 8/2020
JP 2005-144375 A 6/2005
(Continued)

OTHER PUBLICATIONS

International Search Report issued Aug. 12, 2022, in PCT/JP2022/009434 filed on Mar. 4, 2022, 6 pages.
(Continued)

*Primary Examiner* — Jonathan M Peo
(74) *Attorney, Agent, or Firm* — Oblon, McClelland, Maier & Neustadt, L.L.P.

(57) ABSTRACT

A flow channel structure for removing a foreign substance includes a first flow channel, where the first flow channel has a first region having a depth shallower than a depth of another region. A method for removing a foreign substance in a fluid includes flowing the fluid to the first flow channel of the flow channel structure for removing a foreign substance.

16 Claims, 11 Drawing Sheets

(51) Int. Cl.

| | |
|---|---|
| ***B01F 23/45*** | (2022.01) |
| ***B01F 33/301*** | (2022.01) |
| ***B01F 35/00*** | (2022.01) |

(52) U.S. Cl.

CPC ............ *B01F 23/45* (2022.01); *B01F 33/301* (2022.01); *B01F 35/187* (2022.01); *B01L 2200/0663* (2013.01); *B01L 2300/0681* (2013.01); *B01L 2300/0867* (2013.01); *B01L 2400/084* (2013.01)

(56) References Cited

U.S. PATENT DOCUMENTS

| | | | |
|---|---|---|---|
| 2015/0251181 A1 | 9/2015 | Saito | |
| 2018/0038876 A1 | 2/2018 | Arai | |
| 2018/0266951 A1 * | 9/2018 | Spero | B01L 3/502761 |

FOREIGN PATENT DOCUMENTS

| | | | |
|---|---|---|---|
| JP | 2008-51803 | A | 3/2008 |
| JP | 2015-166707 | A | 9/2015 |
| JP | 2020-72708 | A | 5/2020 |
| JP | 2022-167074 | A | 11/2022 |
| WO | WO 2020/097048 | A1 | 5/2020 |
| WO | WO 2022/224595 | A1 | 10/2022 |

OTHER PUBLICATIONS

Isokawa, M., et al. "Liquid Chromatography Chip with Low-Dispersion and Low-Pressure-Drop Turn Structure Utilizing a Distribution-Controlled Pillar Array" Analytical Chemistry (vol. 88, No. 12), 2016, pp. 6485-6491, DOI: 10.1021/acs.analchem.6b01201.

Stroock, A., et al. "Chaotic Mixer for Microchannels" Science (vol. 295, No. 5555), 2002, pp. 647-651, DOI: 10.1126/science.1066238.

Japanese Office Action issued May 7, 2024 in Japanese Patent Application No. 2021-091332 (with unedited computer-generated English Translation), 8 pages.

Combined Chinese Office Action and Search Report issued Apr. 22, 2025 in Chinese Patent Application No. 202280005778.4, (with unedited computer-generated English translation), 21 pages.

* cited by examiner

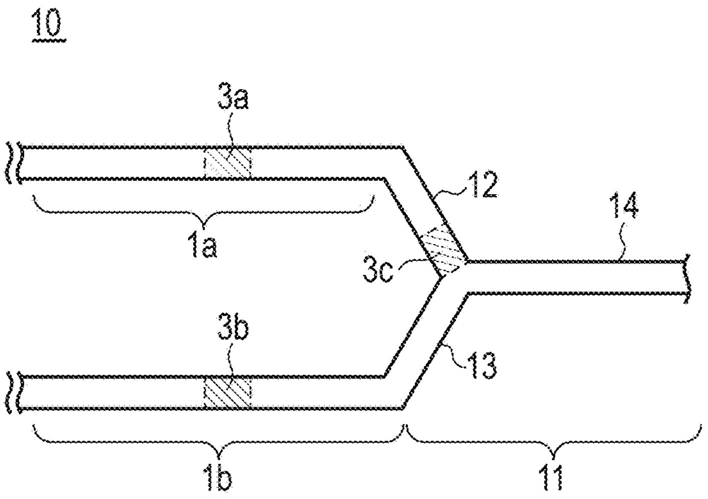
F I G. 3
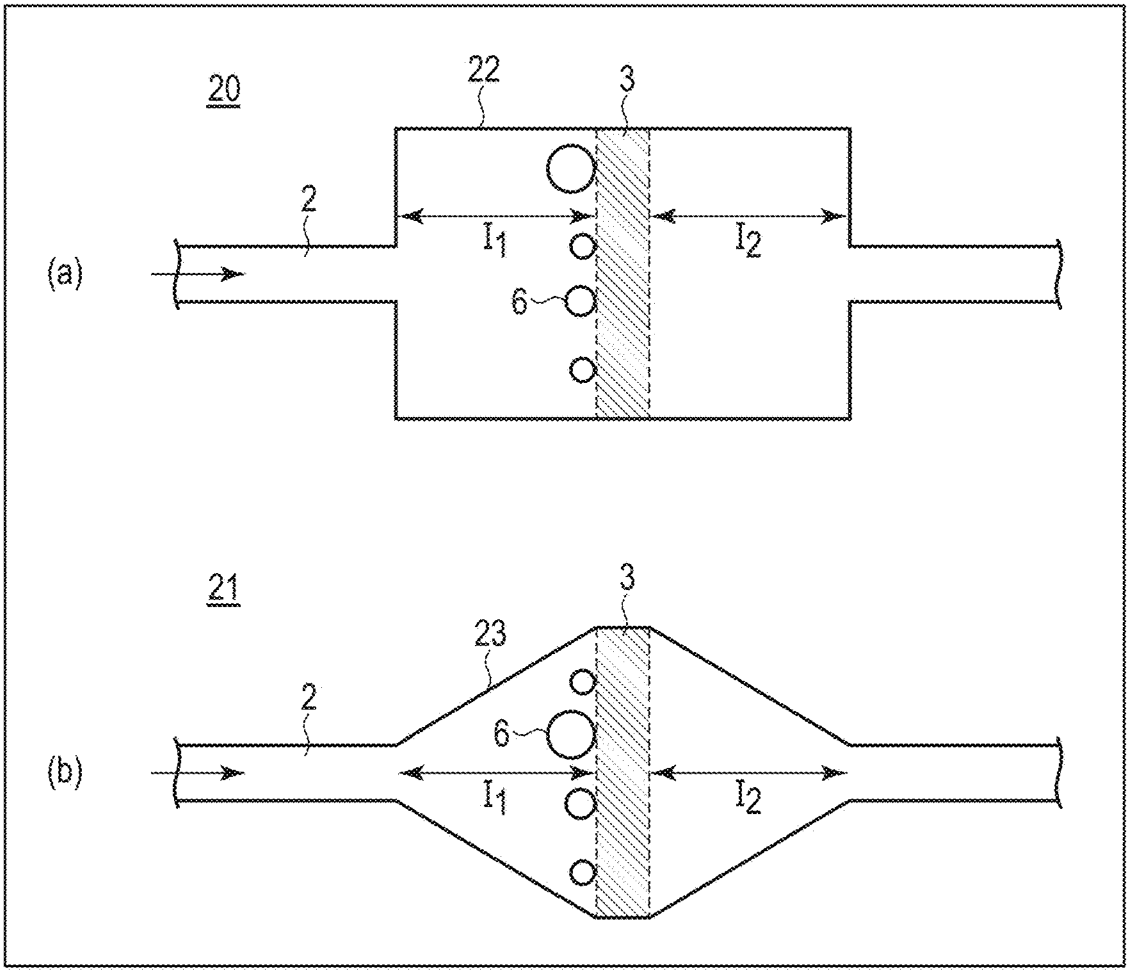
F I G. 4

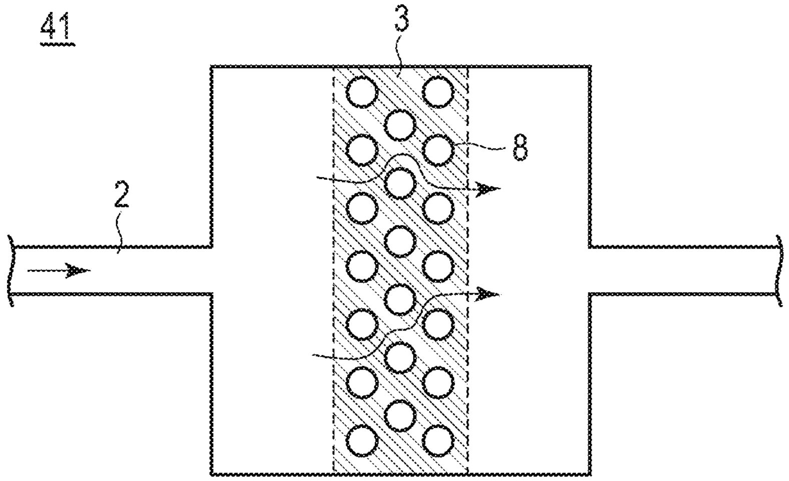
F I G. 8
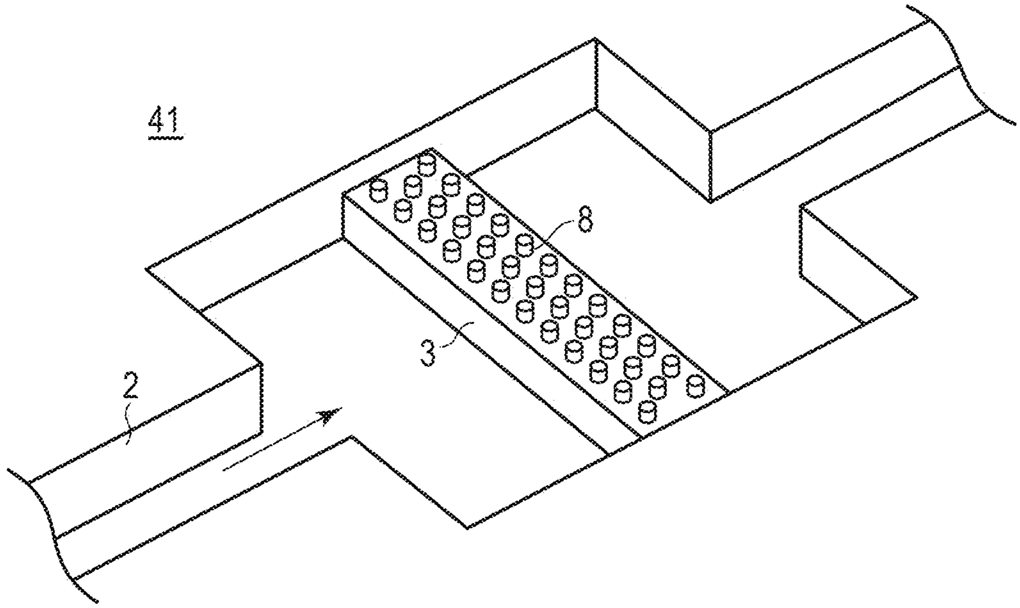
F I G. 9

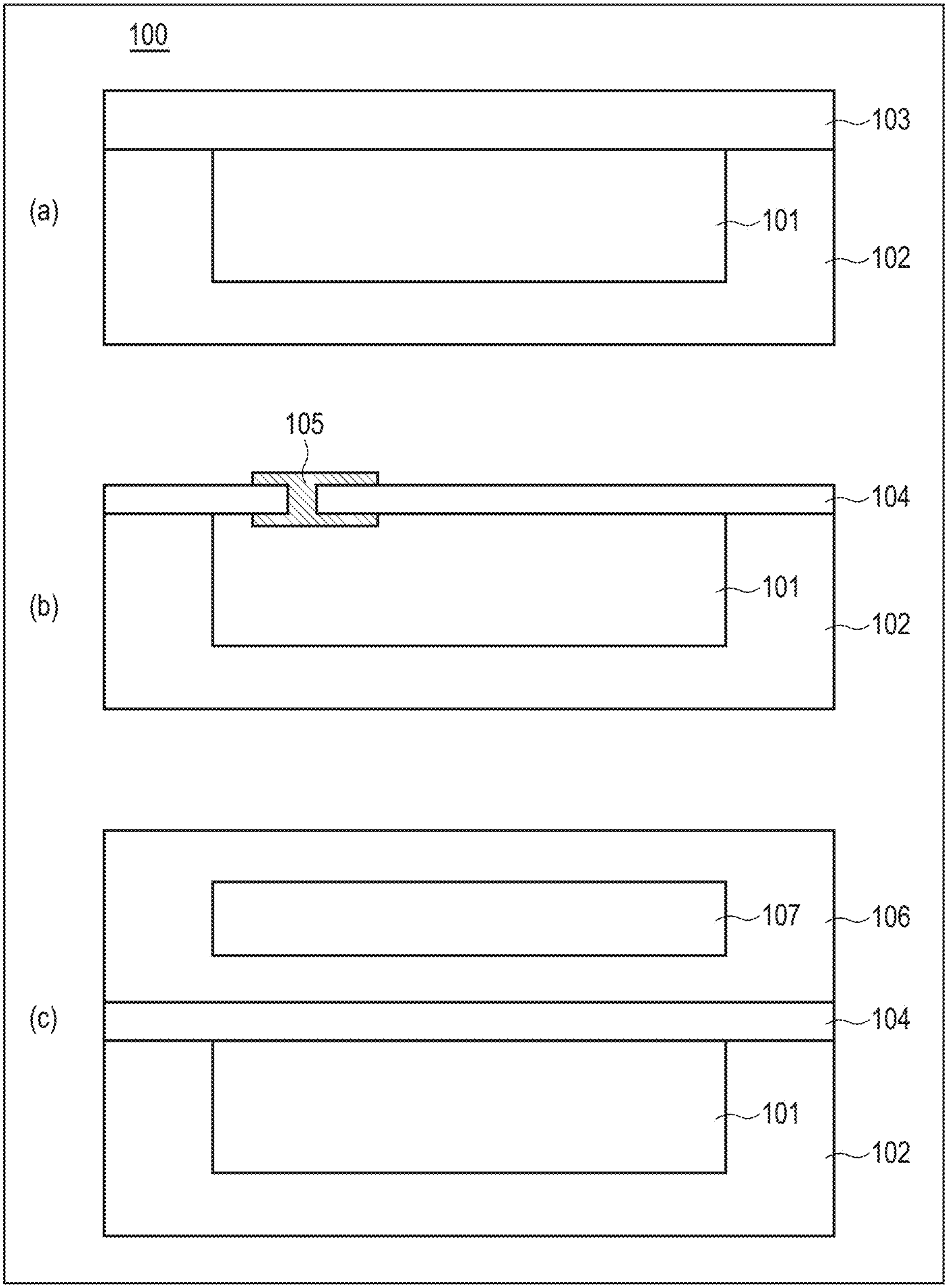
F I G. 11

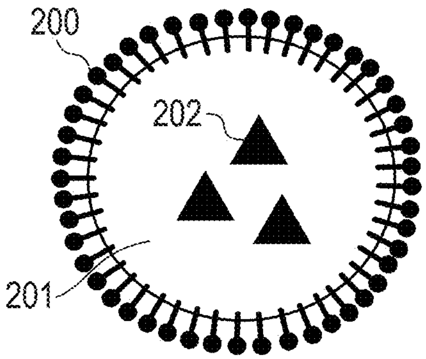
F I G. 12
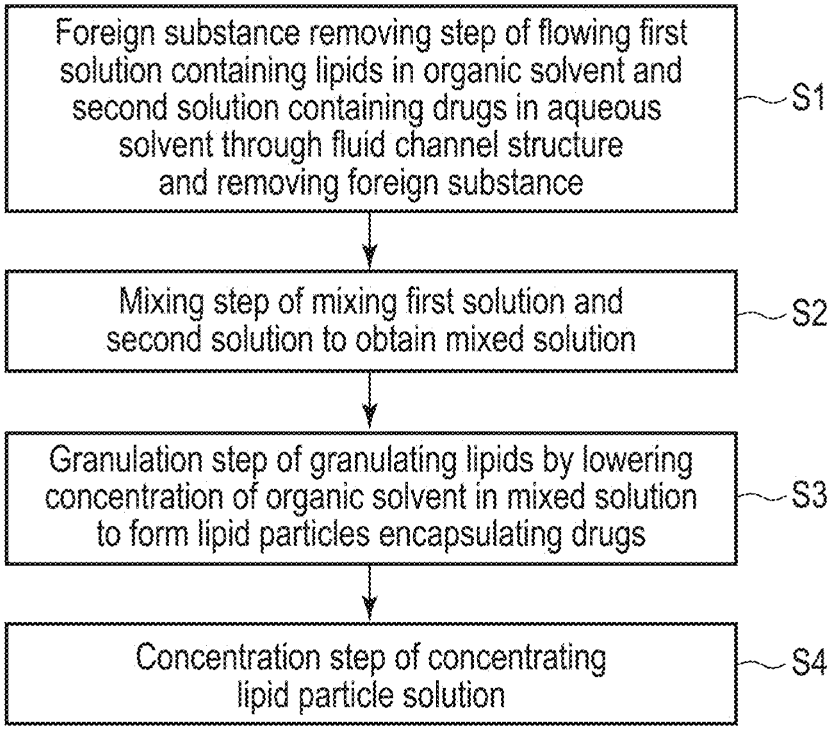
F I G. 13

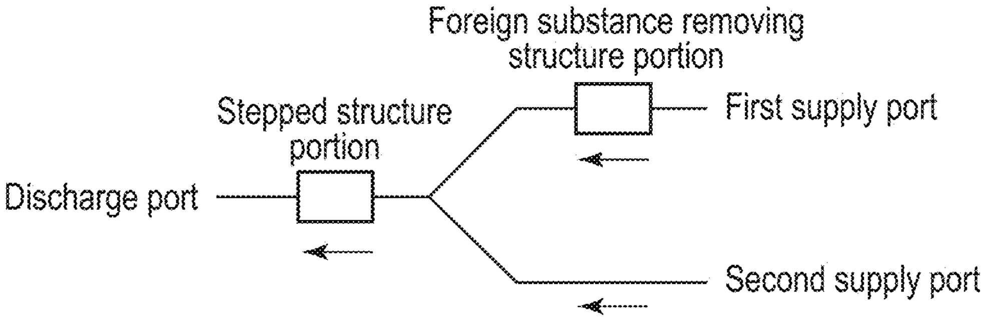
F I G. 15

FLOW CHANNEL STRUCTURE FOR REMOVING FOREIGN SUBSTANCE, METHOD FOR REMOVING FOREIGN SUBSTANCE, AND METHOD FOR MANUFACTURING LIPID PARTICLES

CROSS REFERENCE TO RELATED APPLICATIONS

This application is a Continuation Application of PCT Application No. PCT/JP2022/009434, filed Mar. 4, 2022 and published Dec. 8, 2022, and based upon and claiming the benefit of priority from Japanese Patent Application No. 2021-091332, filed May 31, 2021 and published Oct. 15, 2024, the entire contents of all of which are incorporated herein by reference.

FIELD

Embodiments described herein relate generally to a flow channel structure for removing a foreign substance, a method for removing a foreign substance, and a method for manufacturing lipid particles.

BACKGROUND

In a technique for treating a fluid using a micro flow channel, various flow channel shapes have been devised for various purposes such as mixing of fluids, and addition or removal of substances. In such a flow channel, it is important that the effect by the shape can be exhibited as designed. One of the factors that inhibit this is mixing of a foreign substance. There is also a method for filtering a fluid with a filter in advance for removing a foreign substance, but contamination due to filter installation and a complicated structure are concerned. For example, in a case where the frequency of generation of a foreign substance is low, it can be more efficient not to use the filter in consideration of the influence of use of the filter as described above. However, a small foreign substance often affects the effect of the flow channel structure. Therefore, it is required to develop a flow channel structure that reduces the influence of the foreign substance without using a filter.

In addition, a micro flow channel used in a situation where it is desired to avoid contamination, such as a medical use, is preferably a disposable product. However, in order to perform various operations in the micro flow channel, a complicated structure is required, and in addition, since manufacturing of a micro flow channel chip requires precision, it is difficult to reduce a cost. Therefore, a low-cost micro flow channel chip is required.

BRIEF DESCRIPTION OF THE DRAWINGS

FIG. 3 is a plan view illustrating an example of the flow channel structure of the first embodiment connected to an upstream of a mixing flow channel.

FIG. 4 is a plan view illustrating an example of a flow channel structure of a second embodiment.

FIG. 8 is a plan view illustrating an example of the flow channel structure of the fourth embodiment.

FIG. 9 is a perspective view illustrating an example of the flow channel structure of the fourth embodiment.

FIG. 11 is a cross-sectional view illustrating an example of the flow channel structure of the embodiment.

FIG. 12 is a cross-sectional view illustrating an example of lipid particles of an embodiment.

FIG. 13 is a flowchart illustrating an example of a method for manufacturing lipid particles of an embodiment.

FIG. 15 is a block diagram illustrating a configuration of a flow channel structure used in an experiment of an Example.

DETAILED DESCRIPTION

Figure 1:
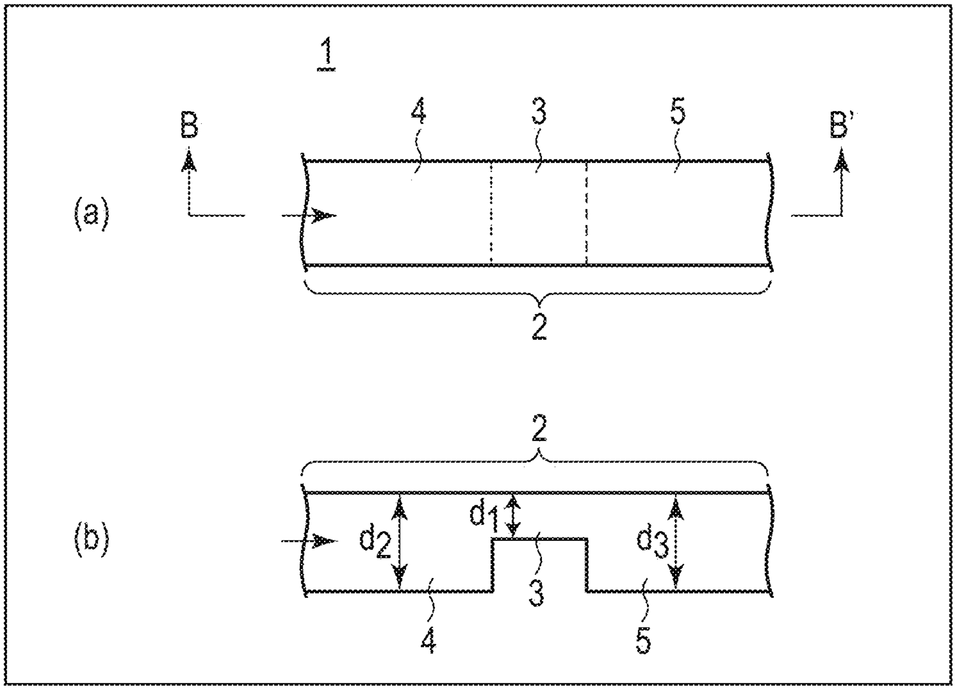
FIG. 1 is a plan view and a cross-sectional view illustrating an example of a flow channel structure of a first embodiment.

In general, according to one embodiment, a flow channel structure for removing a foreign substance includes a first flow channel, and the first flow channel has a first region having a depth shallower than a depth of another region.

Hereinafter, embodiments will be described with reference to the accompanying drawings. Note that, in each of the embodiments, substantially the same constituents are denoted by the same reference numerals, and the description thereof may be partially omitted. The drawings are schematic, and a relationship between a thickness and a planar dimension of each part, a thickness ratio of each part, and the like may differ from actual ones.

Flow Channel Structure for Removing Foreign Substance

A flow channel structure for removing a foreign substance according to an embodiment has a configuration for capturing a foreign substance in a flow channel. Therefore, the foreign substance in a fluid is removed, and the foreign substance can be suppressed from flowing downstream. Note that, in the present specification, "capturing" does not necessarily mean capturing all the foreign substances contained in the fluid, and includes capturing some of the foreign substances. Therefore, the flow channel structure for removing a foreign substance according to the embodiment does not necessarily remove all the foreign substances, and can remove at least some of the foreign substances. Hereinafter, the flow channel structure for removing a foreign substance is also simply referred to as a "flow channel structure of the embodiment" or a "flow channel structure".

Hereinafter, some embodiments of the flow channel structure for removing a foreign substance will be described.

First Embodiment

As illustrated in a plan view of part (a) of FIG. 1, a flow channel structure 1 of a first embodiment includes a first flow channel 2. Here, the first flow channel 2 is a cavity formed inside the flow channel structure 1, that is, a top surface thereof has a lid and is configured in a liquid-tight manner. For example, the first flow channel 2 is a micro flow channel. Note that, in the present drawing, a moving direction of a fluid is indicated by an arrow.

The first flow channel 2 has a first region having a depth shallower than a depth of another region. The first region is hereinafter also referred to as a shallow portion 3. Part (b) of FIG. 1 illustrates a cross-sectional view taken along line B-B' in part (a) of FIG. 1. In the shallow portion 3, for example, a bottom surface protrudes toward a top surface. Therefore, a depth $d_1$ of the shallow portion 3 is shallower than a depth $d_2$ of a region located on an upstream of the shallow portion 3 (hereinafter, also referred to as an "upstream deep portion 4"). The depth $d_2$ of the upstream deep portion 4 and a depth $d_3$ of a region located on a downstream of the shallow portion 3 (hereinafter, also referred to as a "downstream deep portion 5") may be approximately the same.

Figure 2:
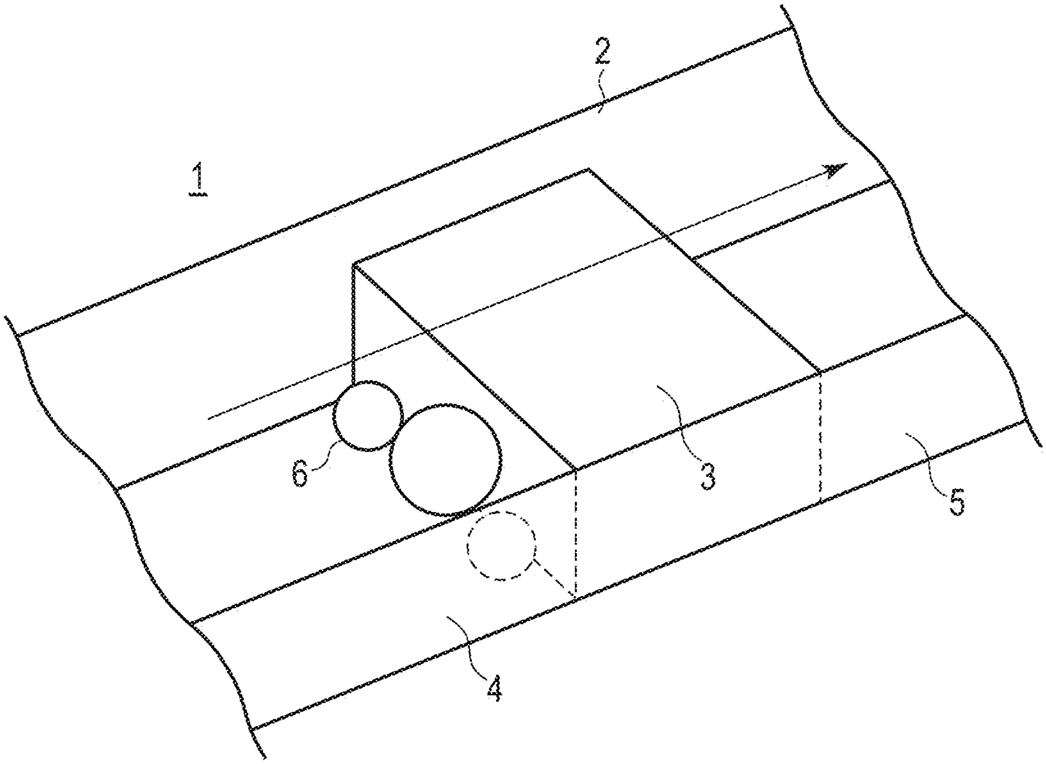
FIG. 2 is a perspective view illustrating an example of the flow channel structure of the first embodiment.

FIG. 2 illustrates a state when a fluid flows through the flow channel structure 1. An arrow indicates a moving direction of the fluid. When the fluid passes through the shallow portion 3, a foreign substance 6 larger than the depth $d_1$ of the shallow portion 3 cannot enter the shallow portion 3 and is captured immediately in front of the shallow portion 3. Accordingly, it is possible to prevent the foreign substance 6 from flowing downstream.

The depth $d_1$ of the shallow portion 3 is not limited. For example, in a case where the foreign substance 6 having a specific size or shape adversely affects the effect of a flow channel structure further provided on a downstream of the flow channel structure 1, the depth $d_1$ is set to a depth at which the foreign substance 6 having the size or shape can be captured.

An example of a method for setting the depth $d_1$ of the shallow portion 3 will be described using an example in which the flow channel structure 1 of the embodiment is provided on an upstream of a two-liquid mixing flow channel structure for mixing two liquids. For example, a flow channel structure 10 illustrated in a plan view of FIG. 3 includes two flow channel structures 1*a* and 1*b* for removing a foreign substance, and a two-liquid mixing flow channel structure 11 having a Y-shape in which a second flow channel 12 connected to a downstream of one flow channel structure 1*a* and a third flow channel 13 connected to a downstream of the other flow channel structure 1*b* join a fourth flow channel 14. Note that a pattern of an oblique line in the drawing indicates a shallow portion (the same applies to the following drawings).

The second flow channel 12 has a second region having a depth shallower than a depth of the fourth flow channel 14 (hereinafter, referred to as a "shallow portion 3*c*") at an end thereof close to the fourth flow channel 14. The shallow portion 3*c* has a function of generating a vortex in the fluid when two liquids are joined in the fourth flow channel 14. The vortex promotes mixing and agitating two fluids.

The fluid from which the foreign substance 6 is removed through the flow channel structure 1*a* is supplied to the second flow channel 12, and the fluid from which the foreign substance 6 is removed through the flow channel structure 1*b* is supplied to the third flow channel 13. In a case where the foreign substance 6 enters the second flow channel 12 and is captured in the shallow portion 3*c* without providing the flow channel structure 1*a* of the embodiment, the foreign substance 6 is stopped in the shallow portion 3*c* of the second flow channel 12, such that the flow channel can be blocked. In addition, even when the flow channel is not completely blocked by the foreign substance 6, the foreign substance 6 inhibits generation of a vortex, and the mixing function can be deteriorated.

In a case where the purpose is to prevent an inflow of the foreign substance 6 having a size in which it is stopped at the shallow portion 3*c*, the depth $d_1$ of the shallow portion 3*a* of the flow channel structure 1*a* is preferably equal to or less than that of the shallow portion 3*c*. Here, "equal" includes a case where a difference is ±0.01 mm in consideration of operational accuracy. For example, when the depth of the fourth flow channel 14 is 0.3 mm and the depth of the shallow portion 3*c* is 0.1 mm, which is ⅓ of the depth of the fourth flow channel 14, a depth $d_1$ of a shallow portion 3*a* is preferably 0.1 mm or less. As described above, by installing the flow channel structure 1*a* including the shallow portion 3*a* having a depth equal to or less than the depth of the shallow portion 3*c* of the two-liquid mixing flow channel structure 11, it is possible to easily prevent the entry of the foreign substance 6 and flow the fluid from which the foreign substance 6 is removed to the two-liquid mixing flow channel structure 11.

On the other hand, in a case where there is a small foreign substance 6 passing through the shallow portion 3*a*, the foreign substance 6 is unlikely to clog the shallow portion 3*c*, and thus may be excluded from consideration. In this case, the depth of the shallow portion 3*a* may be similar to that of the shallow portion 3*c*. However, in a case where it is preferable to remove the small foreign substance 6 that is less likely to cause clogging in the shallow portion 3*c*, the depth of the shallow portion 3*a* may be shallower than that of the shallow portion 3*c*.

Figure 14:
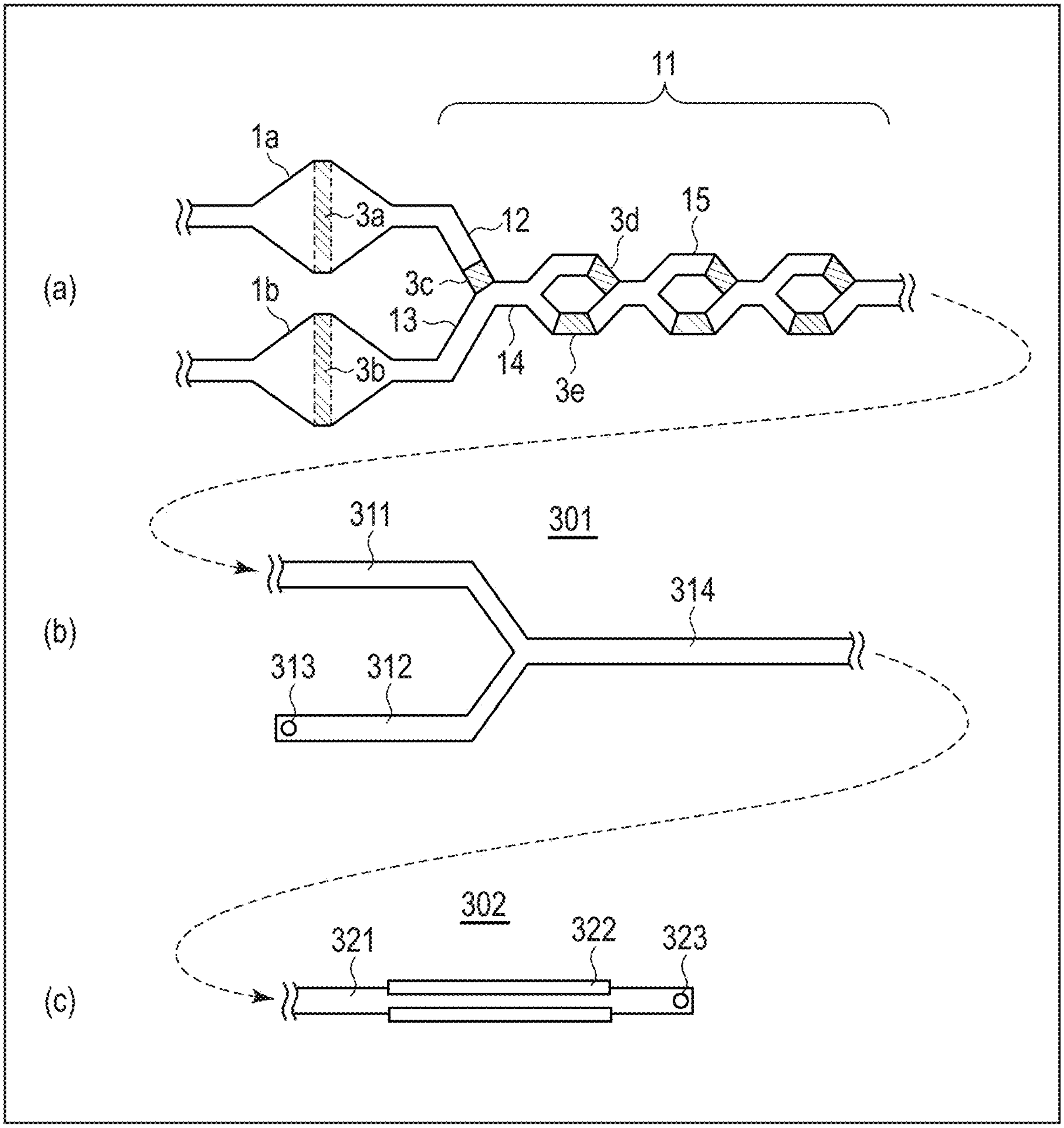
FIG. 14 is a plan view illustrating an example of a flow channel structure for manufacturing lipid particles of an embodiment.

The two-liquid mixing flow channel structure 11 is not limited to this shape, and may have, for example, a T-shape in which the fourth flow channel 14 is simply connected in series to a downstream of the second flow channel 12 to form an integrated linear flow channel, and the third flow channel 13 joins an upstream end of the fourth flow channel 14 at a right angle. In addition, as illustrated in FIG. 14 described below, the two-liquid mixing flow channel structure 11 may further include a flow channel that is connected to a downstream of the fourth flow channel 14 and further mixes and agitates fluids.

As in the example described above, the flow channel structure 1 of the embodiment can be installed on an upstream of a flow channel structure having a certain function and can be used to prevent entry of the foreign substance 6 into the flow channel structure. The flow channel structure in which the flow channel structure 1 is installed is not limited to the two-liquid mixing flow channel structure 11, and can be installed in any flow channel structure in which the entry of the foreign substance 6 can have an adverse effect. In addition, the flow channel structure 1 may be provided in the flow channel through which the fluid in which the foreign substance 6 is expected to exist at that time flows, but it is also preferable to provide the flow channel structure 1 in all the flow channels used to prevent generation and entry of the foreign substance 6 that cannot be expected.

Although the third flow channel 13 is not provided with a shallow portion, it is preferable to provide the flow channel structure 1*b* in order to prevent entry of the foreign substance 6. For example, FIG. 3 does not illustrate a shallow portion such as the shallow portion 3*c* directly connected to the downstream of the shallow portion 3*b*, but in a case of considering a case where the shallow portion is further arranged on the downstream of the fourth flow channel 14 as illustrated in FIG. 14 described below, it is preferable to provide the shallow portion in both of the flow channel structures 1*a* and 1*b*.

In general, since the depth $d_1$ of the shallow portion 3 is set according to the purpose as described above, the depth $d_1$ is not limited, but may be, for example, shallower than the depth $d_2$ of the upstream deep portion 4, and preferably less than ½ of the depth $d_2$, and may be ⅓, ¼, ⅕, or the like, of the depth $d_2$.

In addition, since accuracy of mold forming or cutting that is a preferred method used for manufacturing the present flow channel structure 1 is generally 5 μm, in order to avoid the blockage of the flow channel due to an error, it is desirable that the depth $d_1$ of the shallow portion 3 is at least 10 μm or more.

A length of the shallow portion 3 in a flow direction of the fluid is preferably the same as a flow channel width of the first flow channel 2. Alternatively, the length may be shorter than this as long as it can be manufactured.

The flow channel widths and depths of the upstream deep portion 4 and the downstream deep portion 5, and the amount of fluid supplied are not limited and are determined according to the type of the fluid. In the case of the foreign substance 6 having a thickness (0.1 mm to 0.2 mm) equal to or less than the thickness of the hair, which is generally referred to as the limit with the naked eye, it is difficult for a user of the flow channel to immediately notice the foreign substance 6. Therefore, an application of the present structure is particularly desirable in a normal micro flow channel (for example, the width and depth are about 3 mm or less) in which mixing of a foreign substance of 0.2 mm or less is likely to cause a significant problem.

On the other hand, in a case where a pump is used in the present flow channel structure, it is preferable to use a pump that does not cause pulsation. As such a pump, a pump having a feeding amount of liquid of about 1 ml/sec can be easily available. In consideration of this, an appropriate upper limit of each of a width and a depth of a cross section of each of the upstream deep portion 4 and the downstream deep portion 5 may be about 3 mm.

For example, the depth and width of each of the cross section of each of the upstream deep portion 4 and the downstream deep portion 5 are preferably 0.1 mm to 3 mm.

A flow velocity of the fluid flowing through the flow channel structure 1 is preferably relatively slow. Therefore, it is possible to reduce the possibility that the foreign substance 6 captured due to a pressure increase in the shallow portion 3 is pushed out and flows downstream. In addition, it is also possible to prevent an increase in pressure resistance when a large amount of foreign substance 6 is captured.

The flow channel structure 1 has such a simple shape in which the shallow portion 3 is provided, and it is possible to remove the foreign substance 6 without using a complicated structure such as a filter. Although the flow channel structure 1 will be described in detail below, the flow channel structure 1 is easy to manufacture and can be reduced in cost.

Second Embodiment

A flow channel structure of a second embodiment includes a shallow portion 3 having a wide width. Here, the width refers to a length of a first flow channel 2 in a direction orthogonal to a flow direction of a fluid.

For example, a flow channel structure 20 illustrated in a plan view of part (a) of FIG. 4 has a configuration in which a wide flow channel width is maintained from a slightly upstream of a shallow portion 3 to a slightly downstream of the shallow portion 3 of the first flow channel 2. In other words, the flow channel structure 20 has a rectangular wide portion 22 including the shallow portion 3.

In addition, for example, in a flow channel structure 21 of part (b) of FIG. 4, a flow channel width gradually expands from a slightly upstream of a first flow channel 2 to a shallow portion 3, the width becomes the widest at the shallow portion 3, and the flow channel width gradually becomes the original width toward a slightly downstream of the shallow portion 3. In other words, the flow channel structure 21 has a diamond-like wide portion 23 having the widest width at the shallow portion 3.

When a length $l_1$ in a flow direction of a fluid from an upstream end of the wide portion 22 or 23 to the shallow portion 3 and a length $l_2$ from the shallow portion 3 to a downstream end of the wide portion 22 or 23 are too long, a dead volume in the entire micro flow channel is increased, and when the lengths are too short, the resistance due to a trapped foreign substance 6 may be significantly increased. Therefore, in order to easily, generally and evenly spread the foreign substance 6, it is desirable that the width of the foreign substance 6 is the same as the width of the wide portion 22. The length $l_1$ and the length $l_2$ may be the same as or different from each other.

By setting the width of the shallow portion 3 wide in this manner, it is possible to suppress an increase in pressure resistance in the shallow portion 3 and to set an average flow velocity in the shallow portion 3 to be equal to or lower than the flow velocity when the fluid is supplied to the first flow channel 2. For example, in order to obtain such a flow velocity, it is preferable that a cross-sectional area of the flow channel of the shallow portion 3 is the same as or larger than that of the upstream deep portion 4. Therefore, when the depth $d_1$ of the shallow portion 3 is 1/n of the depth $d_2$ of the upstream deep portion 4, in a case where the width of the shallow portion 3 is set to n times of the flow channel width of the upstream deep portion 4 (that is, a relationship of $w2=w1\times n$, in which a width of a flow channel located upstream from the wide portion 22 or 23 is w1 and a flow channel width of the wide portion 22 or 23 including the shallow portion 3 is w2), the increase in pressure resistance can be canceled, and the average flow velocity at the shallow portion 3 can be set to the same level.

In addition, according to the embodiment, the foreign substance 6 is dispersed and captured in a width direction, and it is also possible to reduce the possibility that the foreign substance 6 blocks the flow channel.

Third Embodiment

A flow channel structure of a third embodiment has a configuration for collecting and capturing a foreign substance 6 at one location. For example, a flow channel structure 30 illustrated in part (a) of FIG. 5 has a crank-like shape in which a first flow channel 2 is bent at a right angle immediately in front of and immediately behind a shallow portion 3. That is, the flow channel structure 30 includes a front portion 2*a* of the first flow channel 2, the shallow portion 3 connected to one flow channel wall at a downstream end of the front portion 2*a* at a right angle in a flow direction in the front portion 2*a*, and a rear portion 2*b* of the first flow channel connected to a downstream end of the shallow portion 3 at a right angle in a flow direction in the shallow portion 3. A flow direction in the rear portion 2*b* is parallel to and in the same direction as the flow direction in the front portion 2*a*.

The rear portion 2*b* is not necessarily connected at a right angle in the flow direction in the shallow portion 3, and the first flow channel 2 may be bent at a right angle at least immediately in front of the shallow portion 3. For example, the rear portion 2*b* may be connected in series on the extension of the shallow portion 3.

According to this configuration, when a fluid flowing from an upstream of the front portion 2*a* comes into contact with an end of the front portion 2*a* and is bent at a right angle, the foreign substance 6 moves on an extension line of the flow just before it due to its inertia, and thus, is collected and captured at a downstream end of the front portion 2*a*. In addition, by arranging the foreign substance 6 at the end, the flow is bent in front of the end, and the captured foreign substance 6 is prevented from being pushed out to the shallow portion 3.

Figure 5:
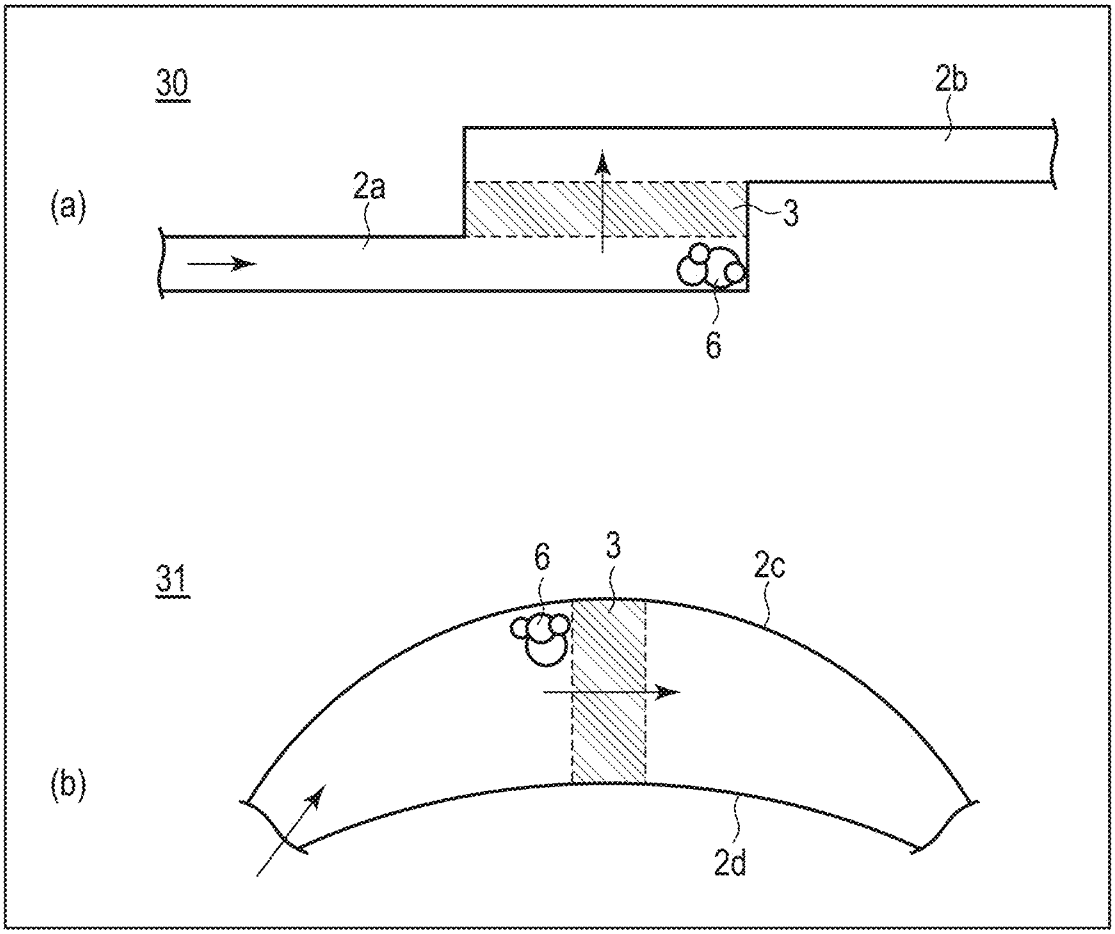
FIG. 5 is a plan view illustrating an example of a flow channel structure of a third embodiment.

In addition, for example, as in a flow channel structure 31 illustrated in part (b) of FIG. 5, a first flow channel 2 is curved in an arc shape, and one flow channel wall 2*c* draws an arc having a curvature larger than that of the other flow channel wall 2*d* facing the flow channel wall 2*c*. Therefore, a foreign substance 6 is collected at an end of a flow channel wall 2*c* having a large curvature.

With the above configuration, the foreign substance 6 is collected at one location, and the fluid smoothly flows in the other region, such that an increase in pressure resistance due to the foreign substance 6 can be alleviated.

Fourth Embodiment

A flow channel structure of a fourth embodiment further includes a structure for filtering a foreign substance 6 (hereinafter, referred to as a "filtering structure"), the structure being provided on a shallow portion 3. For example, an example of a flow channel structure including a plurality of protrusions as a filtering structure will be described with reference to FIGS. 6 to 9.

Figure 6:
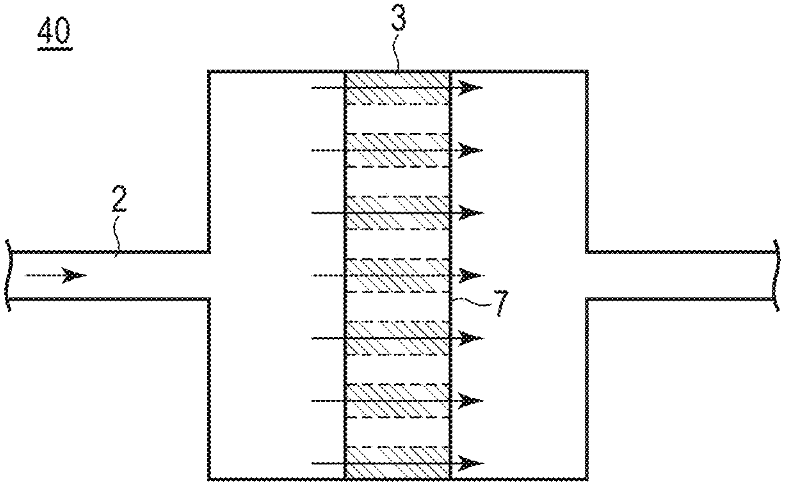
FIG. 6 is a plan view illustrating an example of a flow channel structure of a fourth embodiment.
Figure 7:
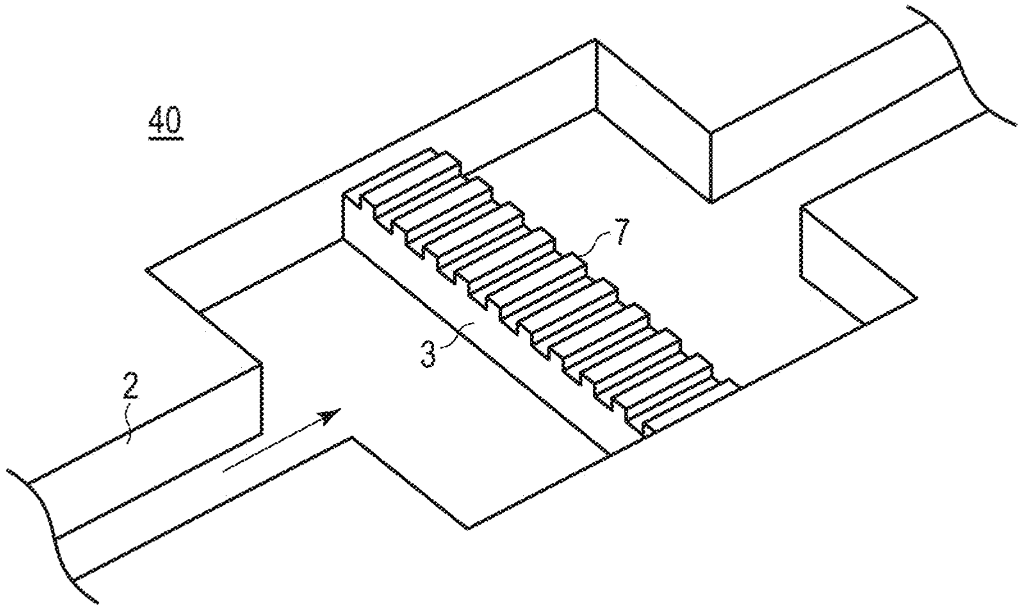
FIG. 7 is a perspective view illustrating an example of the flow channel structure of the fourth embodiment.

A flow channel structure 40 illustrated in a plan view of FIG. 6 and a perspective view of FIG. 7 includes a plurality of elongated protrusions 7 on a shallow portion 3. The plurality of protrusions 7 are arranged at intervals in parallel to each other in a flow direction in a first flow channel 2, for example. The intervals are, for example, equal intervals. The fluid may pass through a gap between the protrusions 7. With this configuration, it is possible to further capture the foreign substance 6 having a size or shape that cannot enter the gap between the protrusions 7. The interval between the protrusions 7 is determined according to the size or shape of the foreign substance 6 to be removed, and is not limited, but from the viewpoint of mass productivity, for example, one width of the shallow portion 3 between the adjacent protrusions is preferably about the same as or more than a depth $d_1$ of the shallow portion 3. A length of the protrusion 7 in a depth direction is not limited, but is preferably about the same as a width of one of the protrusions 7 from the viewpoint of mass productivity, and is not necessarily in contact with a top surface of the first flow channel 2. In addition, the protrusion 7 may not be an elongated rectangular parallelepiped, and may have a meandering shape, a bent shape, a curved shape, or the like. In addition, the length of the protrusion 7 in the flow direction may be the same as that of the shallow portion 3, and may be shorter than the length of the shallow portion 3.

In addition, for example, a flow channel structure 41 illustrated in a plan view of FIG. 8 and a perspective view of FIG. 9 includes a plurality of columnar protrusions 8 extending in a depth direction of a first flow channel 2. The plurality of protrusions 8 are arranged in a staggered manner, for example, in a plane view. The fluid may pass through the shallow portion 3 so as to thread a gap between the protrusions 8. With this configuration, it is possible to further capture a foreign substance 6 having a size or shape that cannot enter the gap between the protrusions 8. An interval or arrangement of the protrusions 8 is determined according to a size or shape of the foreign substance 6 to be removed and is not limited, and may be a random shape or the like instead of a staggered shape. A length of the protrusion 8 in a depth direction is not limited, but is preferably about the same as a diameter of one of the protrusions 8 from the viewpoint of mass productivity, and is not necessarily in contact with a top surface of the first flow channel 2. In addition, the protrusion 8 may not be columnar, and may be a polygonal column, a plate shape, or the like.

The filtering structure can further capture the foreign substance 6. In particular, an elongated foreign substance 6 such as a fiber can be efficiently captured. In addition, in the case of having the filtering structure, since the captured foreign substance 6 is prevented from being pushed out on the shallow portion 3, a flow velocity can be set faster than that in a flow channel structure having no filtering structure.

Fifth Embodiment

Figure 10:
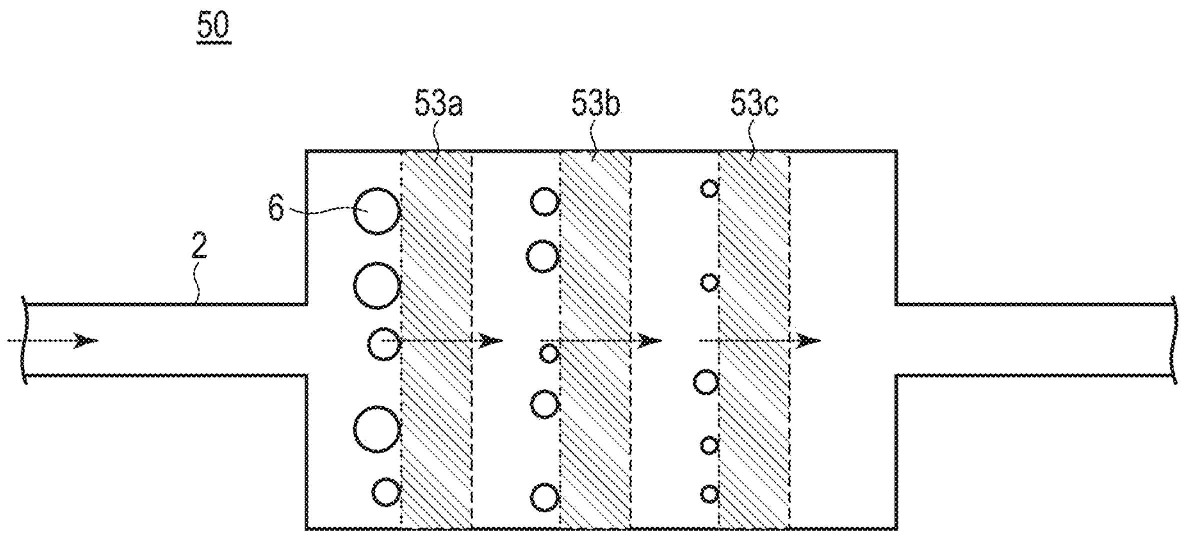
FIG. 10 is a plan view illustrating an example of a flow channel structure of a fifth embodiment.

A flow channel structure of a fifth embodiment includes a plurality of shallow portions 3. For example, a flow channel structure 50 illustrated in FIG. 10 includes three shallow portions, that is, a first shallow portion 53*a*, a second shallow portion 53*b* provided on a downstream of the first shallow portion 53*a*, and a third shallow portion 53*c* provided on downstream of the second shallow portion 53*b*. The first shallow portion 53*a*, the second shallow portion 53*b*, and the second shallow portion 53*c* may have the same or different depths each other. By providing the plurality of shallow portions 3, a foreign substance 6 is likely to be captured, and it is possible to capture a larger amount of foreign substance 6. For example, the foreign substance 6 can be efficiently captured compared with a case of providing one long shallow portion 3. In addition, according to this structure, a depth of a flow channel is changed at each shallow portion, therefore, the flow is directed to the bottom on an immediately downstream of each shallow portion, and a longitudinal vortex may be generated therein. Therefore, it is possible to expect an effect that the smaller foreign substance 6 is gradually captured and removed by the longitudinal vortex.

Method for Manufacturing Flow Channel Structure

A method for manufacturing the flow channel structure of each embodiment (hereinafter, collectively referred to as a "flow channel structure 100") described above will be described below with referent to FIG. 11. As illustrated in part (a) of FIG. 11, the flow channel structure 100 includes, for example, a substrate 102 in which a groove 101 functions as a flow channel is formed, and a plate-shaped lid part 103 bonded to the substrate 102 so that a top surface of the groove 101 is closed.

A material of the substrate 102 may be appropriately selected from resins such as acrylic, polyethylene, and polypropylene resins, glass, ceramic, and a metal, and so on, according to an application. For example, when the flow channel structure 100 is for a medical use, a cycloolefin polymer or the like is also a preferred example. When the flow channel structure is reused several times, glass, ceramic such as quartz is preferable in terms of stability, and when a temperature or the like is to be adjusted, a metal having a surface subjected to a corrosion resistant treatment may be used. The groove 101 can be formed by press processing or cutting using, for example, a mold. At a location corresponding to a shallow portion 3, the groove 101 may be formed or cut shallower than other portions.

As a material of the lid part 103, for example, the same material as that described for the substrate 102 can be used. The lid part 103 may have, for example, a plate shape. Alternatively, as illustrated in part (b) of FIG. 11, a thin film-shaped lid part 104 may be used.

A sensor terminal 105 for monitoring a state of a fluid can be attached to the film-shaped lid part 104. Alternatively, it is also possible to impart various functions or characteristics such as high thermal conductivity and a function of performing a specific treatment on a specific substance to the lid part 104 (not illustrated).

When there is a concern that the lid part 104 may swell due to internal pressure, as illustrated in part (c) of FIG. 11, the swelling may be suppressed by pressing a pressing plate 106 from above the lid part 104. The pressing plate 106 may include a heat medium flow channel 107 for heat exchange arranged therein, an electric terminal (not illustrated) having a sensor function, or the like.

As such, the flow channel structure 100 can be manufactured by a simple procedure of forming the groove 101 with the shallow portion 3 at a bottom height in the substrate 102 and bonding the lid part 103 or 104 to the substrate 102. Therefore, for example, it is unnecessary to form irregularities in both the substrate 102 and the lid part 103 and to precisely align the substrate 102 and the lid part 103, such that mass productivity is significantly high and the flow channel structure can be manufactured at a low cost.

Method for Removing Foreign Substance

According to an embodiment, a method for removing a foreign substance using the flow channel structure of the embodiment is provided. The method for removing a foreign substance includes flowing a fluid to the first flow channel 2 of the flow channel structure of any one of the embodiments described above. As a result, the foreign substance 6 can be captured in the shallow portion 3, and the fluid from which the foreign substance 6 is removed can be supplied downstream.

Method for Manufacturing Lipid Particles Encapsulating Drugs

Hereinafter, a method for manufacturing lipid particles encapsulating drugs using the flow channel structure of the embodiment will be described.

First, lipid particles manufactured by the present method will be described. As illustrated in FIG. 12, each of lipid particles 200 includes a lipid membrane formed by arranging lipid molecules, and has a substantially hollow spherical shape. Drugs 202 are encapsulated in a lumen 201 of the lipid particles 200. The lipid particles 200 may be used, for example, to deliver the drugs 202 into cells.

As illustrated in FIG. 13, the manufacturing method includes, for example, the following steps of: flowing a first solution containing lipids as a material of lipid particles in an organic solvent and a second solution containing drugs in an aqueous solvent to the first flow channel 2 of the flow channel structure of the embodiment and removing a foreign substance in the fluid (foreign substance removing step S1); mixing the first solution and the second solution after the removing of the foreign substance to obtain a mixed solution (mixing step S2); granulating the lipids by lowering a concentration of the organic solvent in the mixed solution to form lipid particles encapsulating drugs (granulation step S3); and concentrating a lipid particle solution (concentration step S4).

Hereinafter, an example of the procedure of the present manufacturing method will be described, and first, the first solution and the second solution will be described.

The first solution contains the lipids in the organic solvent. The lipid is a lipid to be a material constituting the lipid particles 200. The first solution can be prepared by mixing lipids and an organic solvent. The lipid may be, for example, a lipid of a main component of a biological membrane. In addition, the lipid may be artificially synthesized. The lipid may include, for example, a base lipid such as a phospholipid or a sphingolipid such as diacylphosphatidylcholine, diacylphosphatidylethanolamine, ceramide, sphingomyelin, dihydrosphingomyelin, cephalin, or cerebroside, or a combination thereof.

For example, as the base lipid, it is preferable to use 1,2-dioleoyl-sn-glycero-3-phosphoethanolamine (DOPE), 1,2-stearoyl-sn-glycero-3-phosphoethanolamine (DSPE), 1,2-dipalmitoyl-sn-glycero-3-phosphatidylcholine (DPPC), 1-palmitoyl-2-oleoyl-sn-glycero-3-phosphatidylcholine (POPC), 1,2-di-O-octadecyl-3-trimethylammonium-propane (DOTMA), 1,2-dioleoyl-3-dimethylammonium-propane (DODAP), 1,2-dimyristoyl-3-dimethylammonium-propane (14:0 DAP), 1,2-dipalmitoyl-3-dimethylammonium-propane (16:0 DAP), 1,2-distearoyl-3-dimethylammonium-propane (18:0 DAP), N-(4-carboxybenzyl)-N,N-dimethyl-2,3-bis(oleoyloxy)propane (DOBAQ), 1,2-dioleoyl-3-trimethylammonium-propane (DOTAP), 1,2-dioleoyl-sn-glycero-3-phosphocholine (DOPC), 1,2-dilauroyl-sn-glycero-3-phosphocholine (DLPC), 1,2-dioleoyl-sn-glycero-3-phospho-L-serine (DOPS), or cholesterol, or a combination thereof. In particular, it is preferable to use DOTAP and/or DOPE.

It is preferable that the lipid further contains a first lipid compound and/or a second lipid compound that are biodegradable lipids. The first lipid compound can be represented by the formula Q-$CHR_2$. (In the formula, Q is a nitrogen-containing aliphatic group which contains two or more tertiary nitrogens and no oxygen, Rs are each independently a $C_{12}$ to $C_{24}$ aliphatic group, and at least one R contains a linking group LR selected from the group consisting of —C(═O)—O—, —O—C(═O)—, —O—C(═O)—O—, —S—C(═O)—, —C(═O)—S—, —C(═O)—NH—, and —NHC(═O)— in the main chain or side chain thereof.)

The first lipid compound is, for example, a lipid having a structure represented by the following formula.

(1-01)

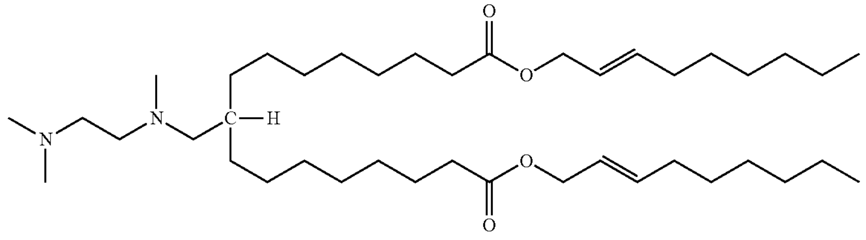

-continued
(1-02)
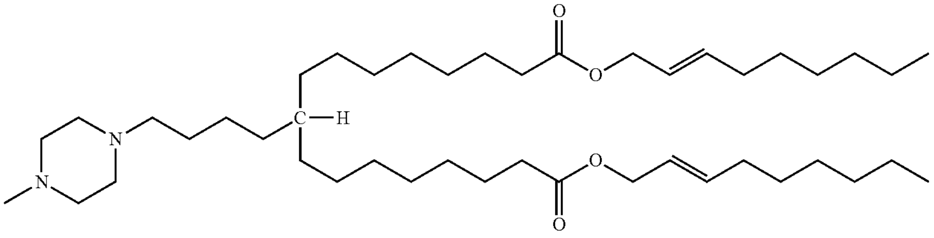
(1-03)
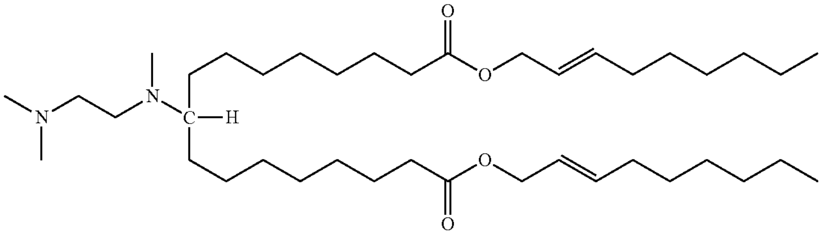
(1-04)
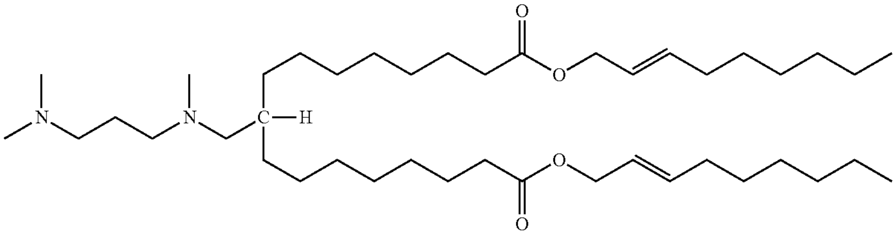
(1-05)
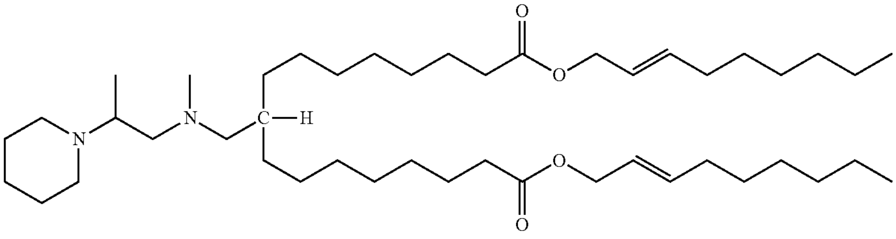
(1-06)
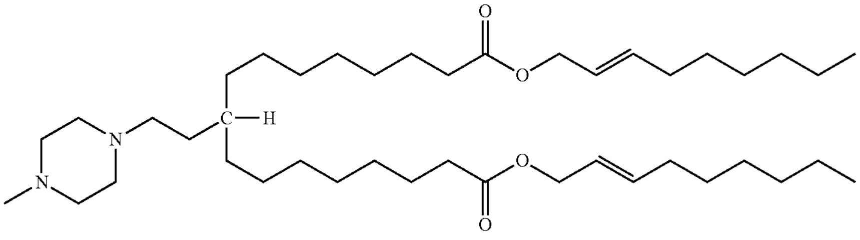
(1-07)
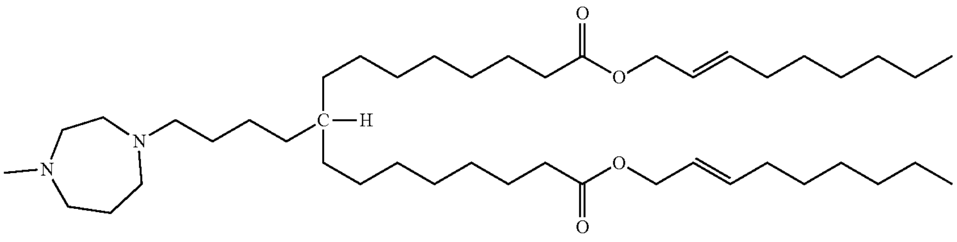

-continued
(1-08)
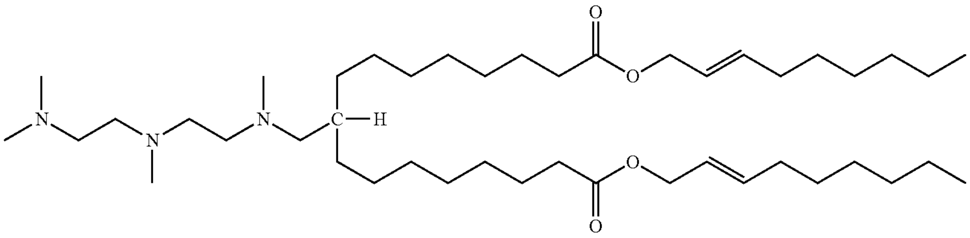
(1-09)
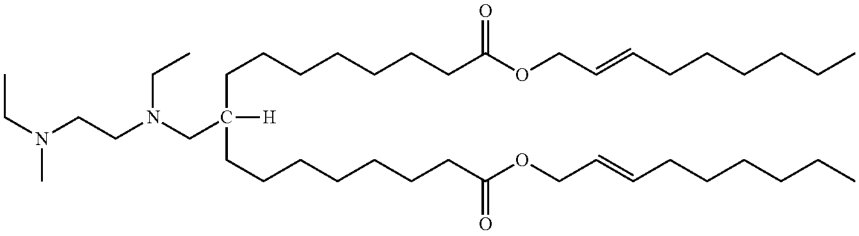
(1-10)
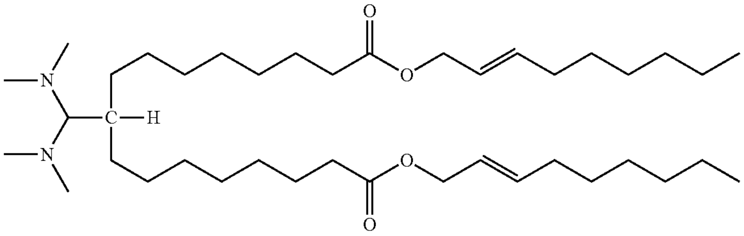
(1-11)
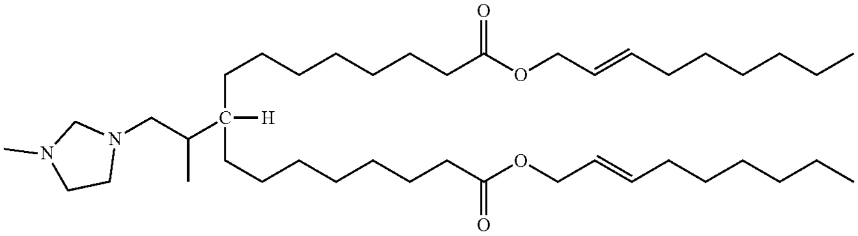
(1-12)
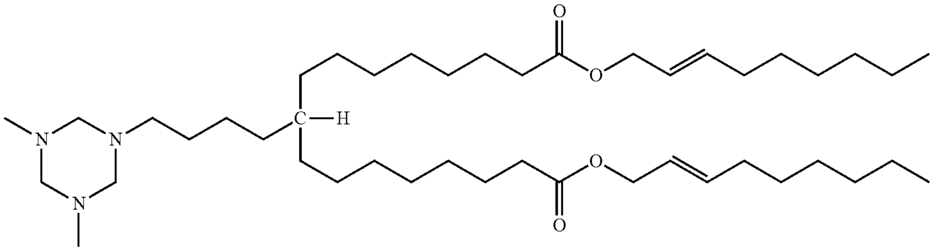
(1-13)
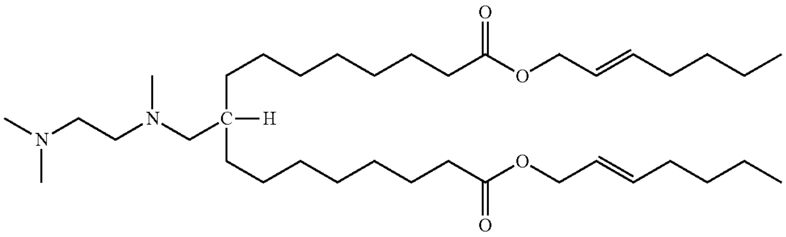

-continued
(1-14)
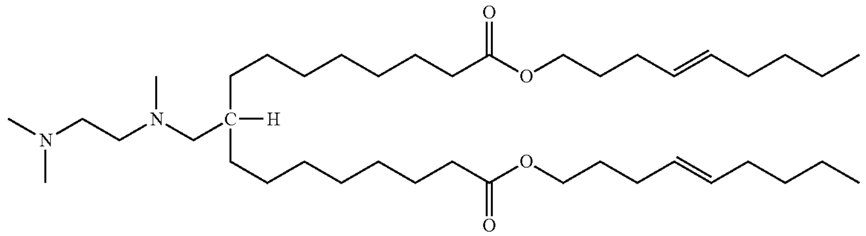
(1-15)
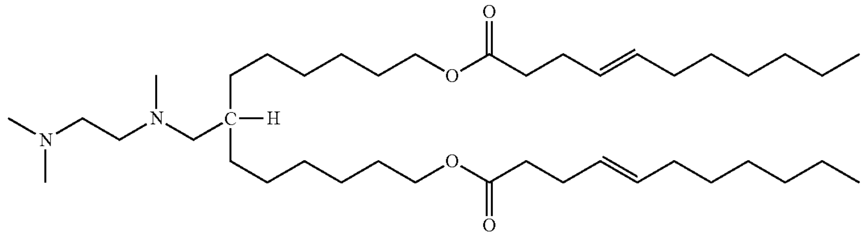
(1-16)
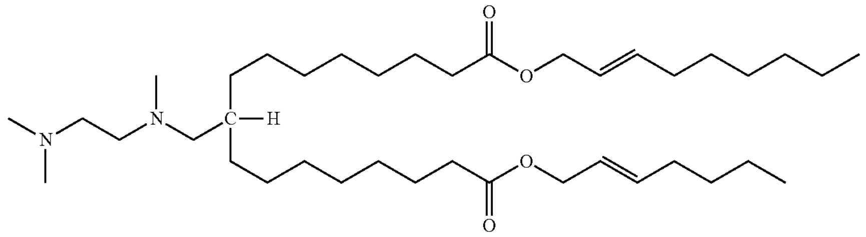
(1-17)
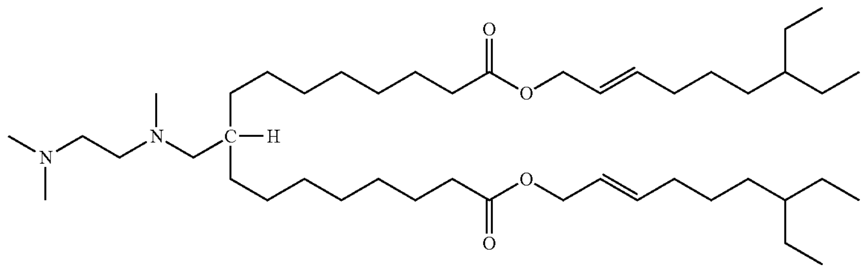
(1-18)
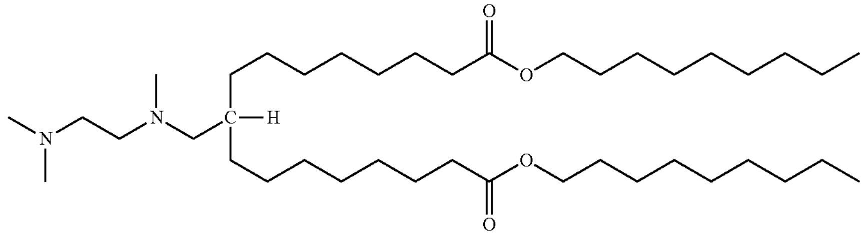
(1-19)
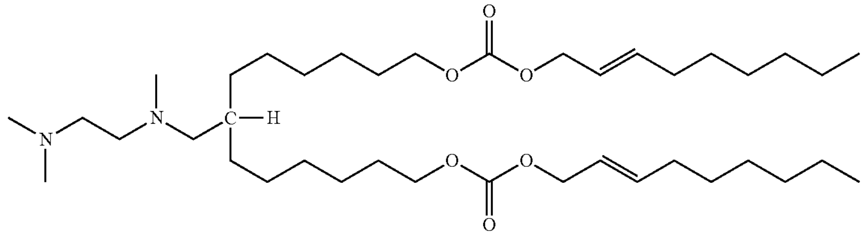

-continued (1-20)

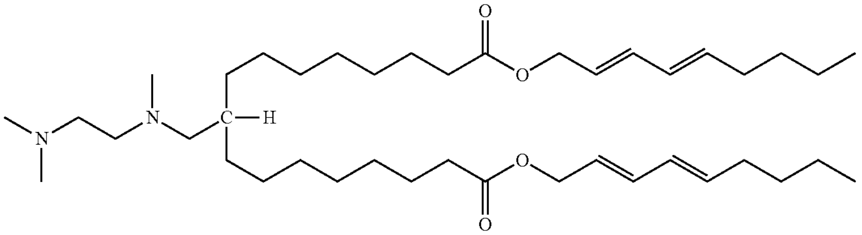

(1-21)

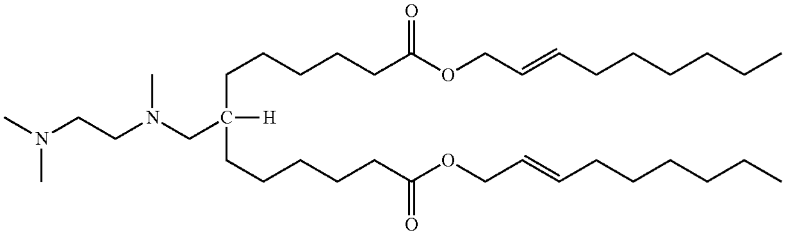

It is particularly preferable to use a lipid compound of Formula (1-01) and/or a lipid compound of Formula (1-02).

The second lipid compound can be represented by the formula P—[X—W—Y—W'—Z]$_2$. (In the formula, P is an alkyleneoxy having one or more ether bonds in the main chain thereof, Xs are each independently a divalent linking group that includes a tertiary amine structure, Ws are each independently a $C_1$ to $C_6$ alkylene, Ys are each independently a divalent linking group selected from the group consisting of a single bond, an ether bond, a carboxylic acid ester bond, a thiocarboxylic acid ester bond, a thioester bond, an amide bond, a carbamate bond, and a urea bond, W's are each independently a single bond or a $C_1$ to $C_6$ alkylene, and Zs are each independently a fat-soluble vitamin residue, a sterol residue, or a $C_{12}$ to $C_{22}$ aliphatic hydrocarbon group.)

The second lipid compound is, for example, a lipid having a structure represented by the following formula.

(2-01)

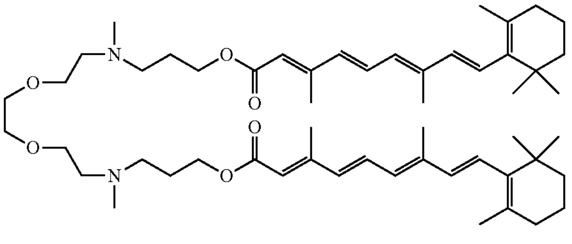

(2-02)

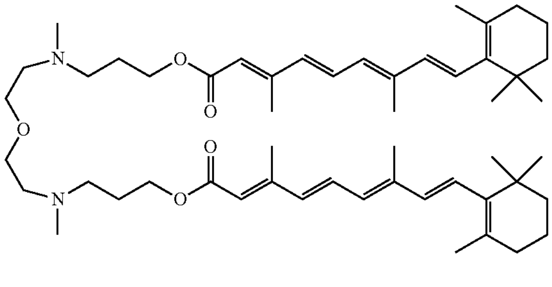

(2-03)

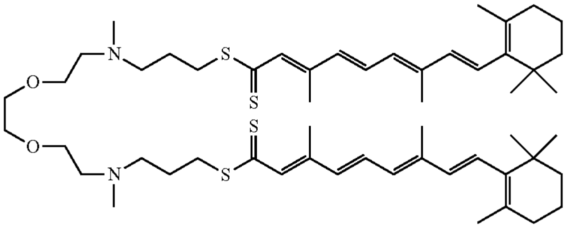

(2-04)

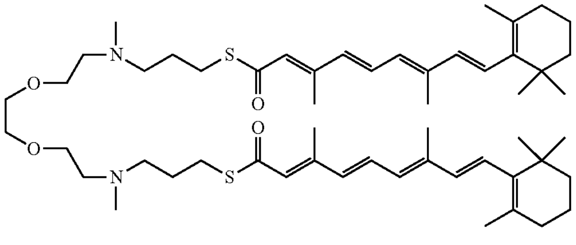

-continued
(2-05)
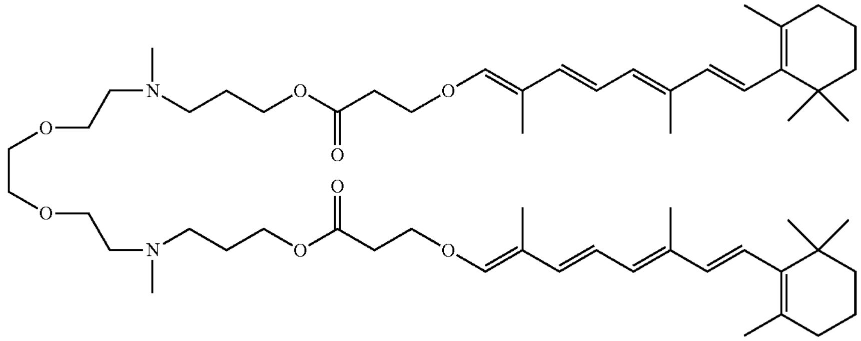
(2-06)
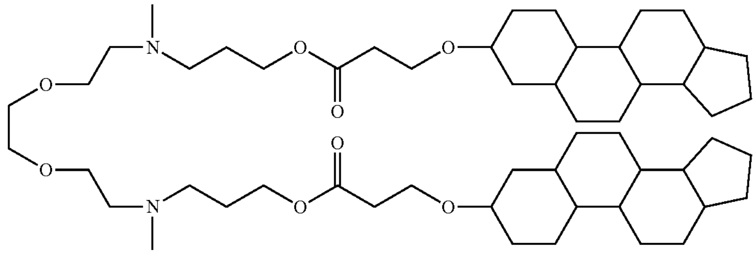
(2-07)
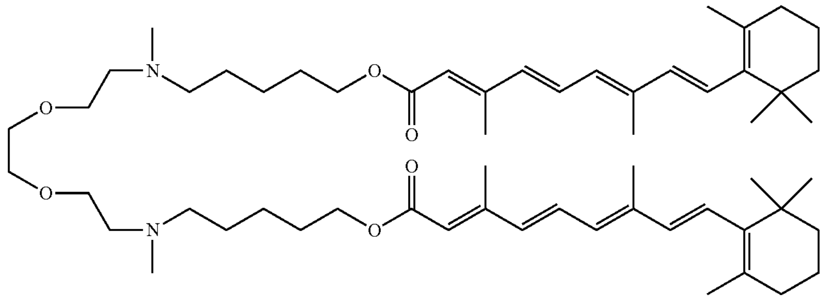
(2-08)
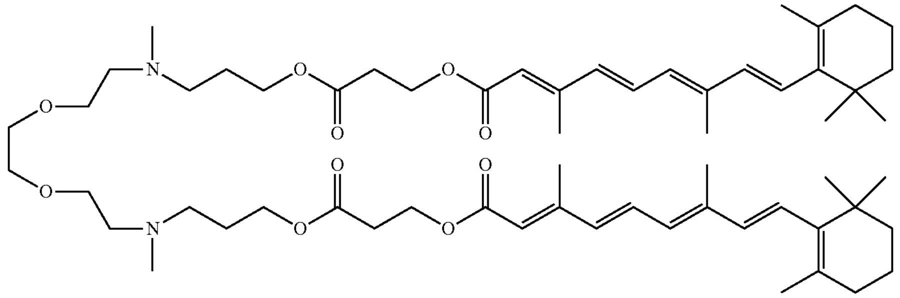
(2-09)
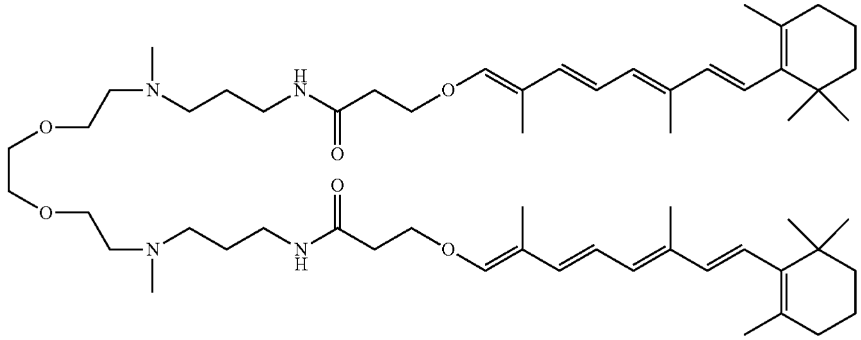

-continued (2-10)

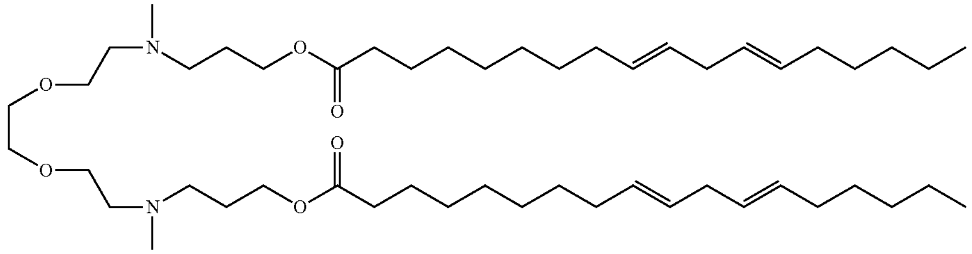

(2-11)

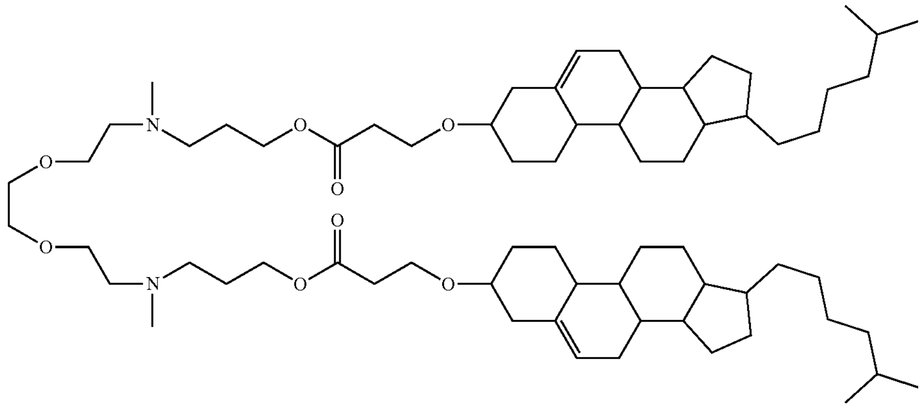

(2-12)

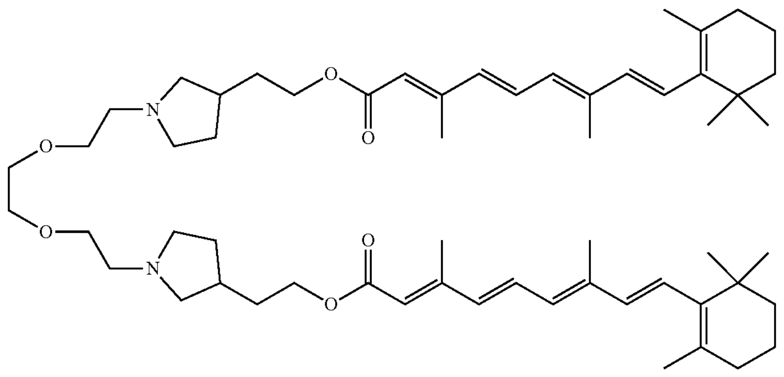

It is particularly preferable to use a compound of Formula (2-01).

In case where the first lipid compound and the second lipid compound are contained, it is possible to increase the amount of drugs 202 encapsulated in the lipid particles 200 and to increase the introduction efficiency of the drugs 202 into cells. In addition, cell death of the cells into which the drugs 202 are introduced can also be decreased. A content of the base lipid is preferably about 30% to about 80% (molar ratio) with respect to the total lipid material. Alternatively, the base lipid may constitute nearly 100% of the lipid material. Contents of the first and second lipid compounds are preferably about 20% to about 70% (molar ratio) with respect to the total lipid material.

It is also preferable that the lipid includes a lipid that prevents flocculation of the lipid particles 200. For example, it is preferable that the lipid that prevents flocculation further contains a PEG-modified lipid, for example, polyethylene glycol (PEG) dimyristoyl glycerol (DMG-PEG), a polyamide oligomer derived from an omega-amino (oligoethylene glycol) alkanic acid monomer (U.S. Pat. No. 6,320,017 B), or monosialoganglioside. The content of such a lipid is preferably about 1% to about 10% (molar ratio) with respect to the total lipid material of the lipid particle 200.

The lipid may further contain a lipid such as a lipid that is relatively less toxic for modulating toxicity; a lipid having a functional group for binding a ligand to the lipid particles 200; and a lipid for suppressing leakage of the encapsulated content, such as sterol including cholesterol. It is particularly preferable to contain cholesterol.

For example, the lipid particles 200 preferably contain a compound of Formula (1-01) or Formula (1-02) and/or a compound of Formula (2-01), DOPE and/or DOTAP, cholesterol, and DMG-PEG.

The type and composition of the lipid are appropriately selected in consideration of the intended acid dissociation constant (pKa) of the lipid particles 200 or the size of the lipid particles 200, the type of the encapsulated content, stability in the cells into which the lipid particles are introduced, and the like. For example, in order to obtain a desired composition of the lipids constituting the lipid particles 200, the composition of the lipid contained in the first solution may be set to the same ratio as the desired composition.

The organic solvent in the first solution is, for example, ethanol, methanol, isopropyl alcohol, ether, chloroform, benzene, acetone, or the like. A concentration of the lipids in the organic solvent is preferably, for example, 0.1% to 0.5% (weight).

The second solution can be prepared by containing the drugs 202 in an aqueous solvent and mixing the drugs 202 with the aqueous solvent.

The aqueous solvent is, for example, water, saline such as physiological saline, an aqueous glycine solution, a buffer solution, or the like, and is selected according to the type of the drug 202.

The drug 202 is not particularly limited, and is, for example, a nucleic acid. The nucleic acid drug 202 is, for example, a nucleic acid containing DNA, RNA, and/or other nucleotides, and may be, for example, mRNA of a specific gene, DNA encoding a gene, DNA or a vector containing a gene expression cassette containing a gene and other sequences such a promoter for expressing a gene, or the like.

In a case where the drug 202 is a nucleic acid, the nucleic acid may be treated with a reagent such as ones that facilitates encapsulation of the nucleic acid in lipid particles and/or a reagent that facilitates expression of a gene contained in the nucleic acid in cells before preparing the second solution. For example, such a treatment can be performed by mixing a solution containing nucleic acids and a solution containing the reagent. Before the treatment, a foreign substance may be removed from each of these solutions by the flow channel structure of the embodiment.

The drug 202 that is not a nucleic acid contains, for example, a protein, a peptide, an amino acid, another organic compound or inorganic compound, or the like, as an active ingredient. The drug 202 may be, for example, a therapeutic drug or diagnostic drug for a disease. However, the drug 202 is not limited thereto, and may be any substance as long as it can be encapsulated in the lipid particles 200.

The drug 202 may further contain, for example, a pH adjuster, an osmotic pressure adjuster, and/or a reagent such as a drug activator, if necessary. The pH adjuster is, for example, an organic acid such as citric acid and a salt thereof. The osmotic pressure adjuster is a sugar, an amino acid, or the like. The drug activator is, for example, a reagent that assists the activity of the active ingredient.

The drug 202 may contain one type of substance or may contain a plurality of substances. A concentration of the drugs 202 in the second solution is preferably, for example, 0.01% to 1.0% (weight).

Next, the procedures of the foreign substance removing step S1, the mixing step S2, the granulation step S3, and the concentration step S4 will be described. The foreign substance removing step S1 to the concentration step S4 can be performed using, for example, the flow channel structure illustrated in FIG. 14. Part (a) of FIG. 14 illustrates the flow channel structures 1*a* and 1*b* of embodiments for performing the foreign substance removing step S1 and the two-liquid mixing flow channel structure 11 for performing the mixing step S2, connected to a downstream thereof, part (b) of FIG. 14 illustrates a granulation flow channel structure 301 having a configuration for performing the granulation step S3, and part (c) of FIG. 14 illustrates a concentration flow channel structure 302 having a configuration for performing the concentration step S4.

Foreign Substance Removing Step S1

In the foreign substance removing step S1, for example, the first solution and the second solution are caused to flow through the flow channel structures 1*a* and 1*b*, respectively. The flow channel structures 1*a* and 1*b* are not limited to those illustrated in FIG. 14, and any of the flow channel structures of the first to fifth embodiments can be used. The flow channel structures 1*a* and 1*b* do not need to have the same shape, and may have different shapes each other. In a case where the foreign substance 6 is present in the first solution and the second solution, the foreign substance 6 is captured in the shallow portions 3*a* and 3*b* by the foreign substance removing step S1, and the fluid from which the foreign substance 6 is removed can be supplied to the two-liquid mixing flow channel structure 11 located on a downstream thereof.

Mixing Step S2

Next, the first solution and the second solution are mixed. The mixing of the first solution and the second solution is performed, for example, using the two-liquid mixing flow channel structure 11 as illustrated in part (a) of FIG. 14. Here, the two-liquid mixing flow channel structure 11 has a shape in which the second flow channel 12 and the third flow channel 13 join the fourth flow channel 14 as in FIG. 3, the second flow channel 12 has the shallow portion 3*c* at the end of the fourth flow channel, and further, a flow channel structure 15 in which one flow channel is branched into two and rejoins is provided on a downstream of the fourth flow channel 14. For example, the flow channel structures 15 are arranged in series. One, two, or four or more flow channel structures 15 may be provided, and the flow channel structures 15 may be arranged in parallel. In addition, each of the two branched flow channels of the flow channel structure 15 has, for example, a shallow portion 3*d* and a shallow portion 3*e* having a shallow depth in the middle thereof. Depths of the shallow portion 3*d* and the shallow portion 3*e* may be the same as that of the shallow portion 3*c*.

For example, the first solution from which the foreign substance is removed flows to the second flow channel 12 from the flow channel structure 1*a*, and the second solution from which the foreign substance is removed flows to the third flow channel 13 from the flow channel structure 1*b*. Therefore, two liquids are joined in the fourth flow channel 14 to obtain a mixed solution. On the contrary, the second solution may flow to the second flow channel 12, and the first solution may flow to the third flow channel 13. The mixed solution can be further mixed and agitated by passing through the flow channel structure 15.

The mixing step S2 is not necessarily performed using a flow channel, and the first solution and the second solution after the foreign substance removing step may be stored in a container and mixed and agitated.

Next, in the granulation step S3, a concentration of the organic solvent in the mixed solution is lowered. For example, it is preferable to relatively lower the concentration of the organic solvent by adding a large amount of aqueous solution to the mixed solution. For example, an aqueous solution that is 3 times larger than the amount of the mixed solution is added to the mixed solution. As the aqueous solution, the same aqueous solvent as that used in the first solution can be used. The lipids are granulated by lowering the concentration of the organic solvent to form the lipid particles 200 encapsulating the drugs 202. As a result, a lipid particle solution containing the lipid particles 200 is obtained.

As illustrated in part (b) of FIG. 14, the granulation flow channel structure 301 for performing the granulation step S3 is, for example, a Y-shaped flow channel. An upstream end of one Y-shaped branched flow channel 311 is connected to, for example, the most downstream end of the two-liquid mixing flow channel structure 11, and the mixed solution is supplied from the flow channel 311. An upstream end of the other flow channel 312 includes, for example, an aqueous solution inlet 313, and the aqueous solution flows from the flow channel 312. As a result, the aqueous solution is mixed with the mixed solution in a flow channel 314 where the flow channel 311 and the flow channel 312 are joined. As a result, the lipids are granulated, and the lipid particles 200 in which the drugs 202 are encapsulated are formed, thereby obtaining the lipid particle solution containing the lipid particles 200.

The granulation step S3 is not necessarily performed using the flow channel, and for example, an aqueous solution may be added to the mixed solution collected in a container.

In this way, the lipid particles 200 can be manufactured.

Concentration Step S4

The concentration step S4 is performed, for example, by removing a part of the solvent and/or excess lipids and drugs 202 from the lipid particle solution. The concentration can be performed, for example, by ultrafiltration. For the ultrafiltration, for example, an ultrafiltration filter having a pore diameter of 2 nm to 100 nm is preferably used. For example, Amicon (registered trademark) Ultra-15 (Merck) or the like can be used as the filter. By performing the concentration step S4, the lipid particle solution having high purity and high concentration can be obtained. A concentration of the lipid particles 200 in the lipid particle solution after the concentration is preferably about $1\times10^{13}$ number/mL to $5\times10^{13}$ number/mL.

As illustrated in part (c) of FIG. 14, the concentration flow channel structure 302 for performing the concentration step S4 includes a flow channel 321 and a filter 322 provided on a wall surface of the flow channel 321. An upstream end of the flow channel 321 is connected to, for example, a flow channel 314 of the granulation flow channel structure 301.

The filter 322 is provided instead of, for example, a part of the wall surface of the flow channel 321. Any of the ultrafiltration filters described above can be used as the filter 322.

For example, when the lipid particle solution flows to the flow channel 321 from the flow channel 314, the remaining material, the excess solvent, and the like pass through the filter 322 and are discharged to the outside of the flow channel 321, and the lipid particles 200 remain in the flow channel 321 and flow downstream. Therefore, the lipid particle solution is concentrated. A downstream end of the flow channel 321 may include a discharge port 323 for collecting the lipid particle solution after the concentration, or may be linked to a tank for collecting the lipid particle solution.

The concentration step S4 is not necessarily performed using the flow channel, and for example, the lipid particle solution collected in the container may be filtered with a filter.

In addition, the method for lipid particles of the embodiment may further include a treatment for improving the quality of the lipid particles 200, if necessary. The improvement of the quality can be, for example, prevention of leakage of the drugs 202 from the lipid particles 200, an increase in amount of drugs 202 encapsulated in the lipid particles 200, an increase in ratio of the lipid particles 200 encapsulating the drugs 202 (encapsulated ratio), a reduction and prevention of flocculation of the lipid particles 200, and/or a reduction in variation in the size of the lipid particles. For example, a treatment for cooling the lipid particle solution may be performed. Such a treatment may also be performed using a flow channel.

Each of the flow channels described above is, for example, a micro flow channel. The flowing of the fluid in the flow channel, the injection of the fluid into the flow channel, the extraction of the fluid from the tank, and/or the accommodation of the lipid particle solution in the container can be performed by, for example, a pump or extrusion mechanism configured and controlled to automatically perform these operations.

In the method for manufacturing lipid particles of the embodiment, it is not always necessary to include the concentration step S4, and the method for manufacturing lipid particles of the embodiment may include at least the foreign substance removing step S1, the mixing step S2, and the granulation step S3.

According to the method for manufacturing lipid particles of the embodiment, since the foreign substance 6 can be removed using the flow channel structure of the embodiment, adverse effects on the mixing step S2, the granulation step S3, and the concentration step S4 caused by the foreign substance are reduced. As a result, it is possible to more efficiently manufacture the high-quality lipid particles 200.

EXAMPLES

An example in which the flow channel structure of the second embodiment is manufactured and used will be described below.

A flow channel structure illustrated in FIG. 15 was manufactured. The flow channel structure has a Y-shaped configuration in which two flow channels are joined in one flow channel. One of the two channels before joining has a foreign substance removing structure portion, and the other flow channel does not have a foreign substance removing structure portion. The foreign substance removing structure portion has a shape illustrated in part (a) of FIG. 16, that is, a shape having the wide shallow portion 3*a* of the second embodiment. The depth of the shallow portion 3*a* was ⅓ of a depth of each of front and rear flow channels, and the width of the shallow portion 3*a* was 3 times the flow channel width of each of the front and rear flow channels. In addition, the flow channel after joining has a stepped structure portion having the configuration illustrated in part (b) of FIG. 16. The stepped structure portion has a configuration in which the flow channel is branched into two and rejoined, and the two branched flow channels each have the shallow portions 3*d* and 3*e* having a shallow depth in the middle thereof. The depths of the shallow portions 3*d* and 3*e* are ⅓ of the depths of the front and rear flow channels. Note that the arrow in the drawing indicates a flow direction of a fluid.

First, the fluid containing the fibrous foreign substance 6 flowed from a first supply port of the flow channel having the foreign substance removing structure portion, and images of the foreign substance removing structure portion and the stepped structure portion were captured. Thereafter, the flow channel was cleaned to remove the foreign substance 6 from the stepped structure portion, the same fluid flowed from a second supply port of the flow channel having no foreign substance removing structure portion, and an image of the stepped structure portion was captured.

Figure 16:
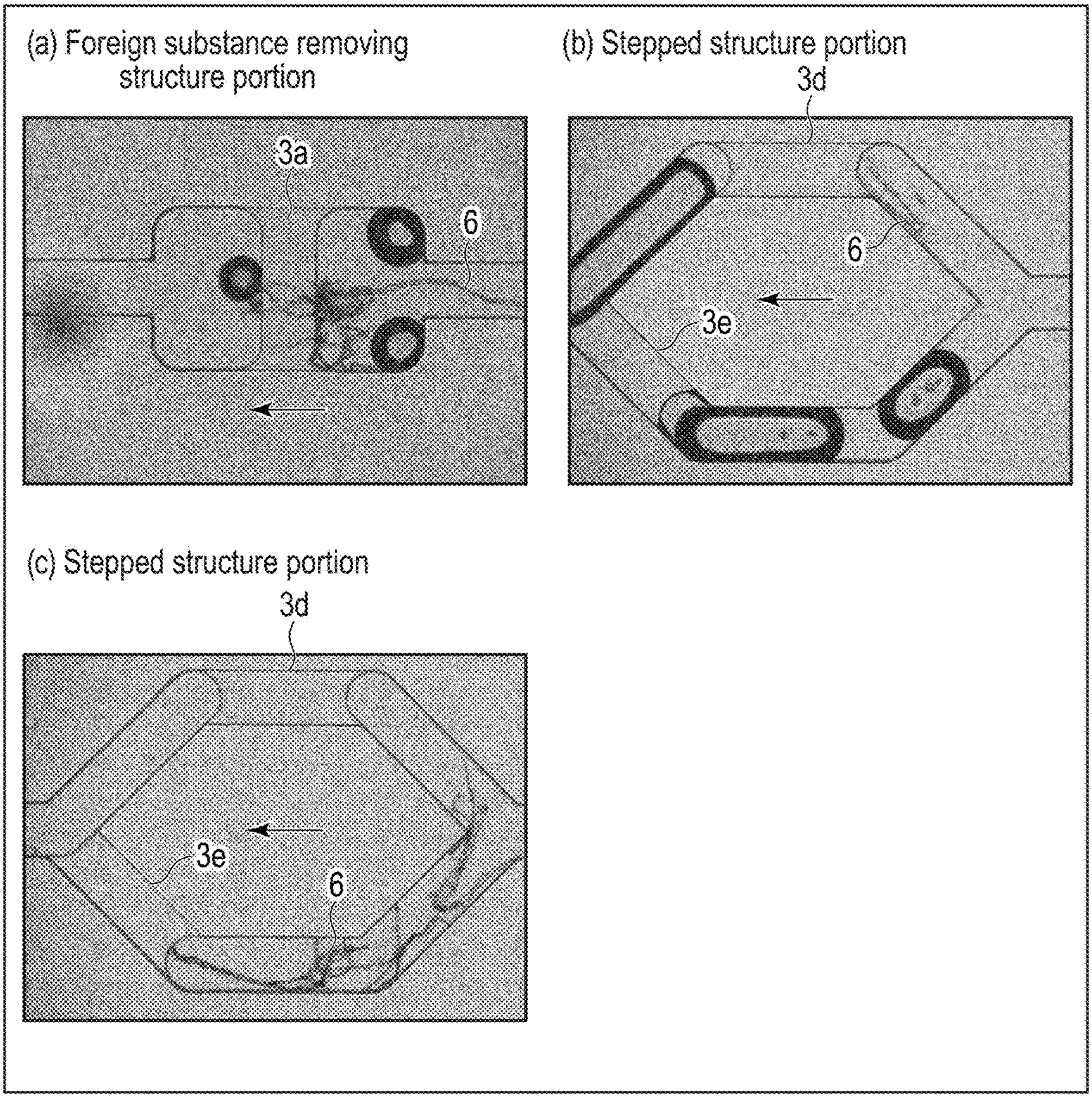
FIG. 16 is a microphotograph showing an experimental result of the Example.

Part (a) of FIG. 16 illustrates a photograph of the foreign substance removing structure portion when the fluid flows from the first supply port. As shown in this photograph, a large amount of foreign substance 6 was captured in the foreign substance removing structure portion. In addition, the photograph of the stepped structure portion at this time is illustrated in part (b) of FIG. 16. As shown in this photograph, a small amount of foreign substance 6 reached the stepped structure portion. Part (c) of FIG. 16 illustrates a photograph of the stepped structure portion when the fluid flows from the second supply port. In this photograph, as compared with part (b) of FIG. 16, a large amount of foreign substance 6 reached the stepped structure portion. Note that black circles seen in the flow channel are bubbles mixed after the test, and are irrelevant to the experimental results.

From the above results, it was clarified that by providing the foreign substance removing structure portion, the amount of foreign substance 6 flowing to the downstream flow channel structure capable of capturing the foreign substance 6 was reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A flow channel structure for removing a foreign substance in each of two liquids and mixes the two liquids, comprising:

partial flow channel structures that remove the foreign substance, each of which has a first flow channel; and a two-liquid mixing flow channel, wherein the first flow channel has a first region having a depth shallower than a depth of another region, wherein the two-liquid mixing flow channel has a shape in which a second flow channel and a third flow channel join a fourth flow channel, wherein the second flow channel is connected to a downstream of one of the partial flow channel structures, wherein the third flow channel is connected to a downstream of an another of the partial flow channel structures, wherein the second flow channel has a second region in which the second flow channel has a depth shallower than a depth of the fourth flow channel at an end of the second flow channel close to the fourth flow channel, and wherein the depth of the first region is less than a depth of the second region.

2. The flow channel structure according to claim 1, wherein the first flow channel is a cavity formed inside the flow channel structure.

3. The flow channel structure according to claim 1, wherein the first region has a flow channel width wider than a flow channel width of the another region.

4. The flow channel structure according to claim 3, wherein the flow channel width of the first region is set so that when a fluid flows to the first flow channel, an average flow velocity of the fluid in the first region is equal to or less than a flow velocity when the fluid is supplied to the first flow channel.

5. The flow channel structure according to claim 1, wherein the first flow channel has a shape bent at a right angle immediately in front of the first region.

6. The flow channel structure according to claim 1, wherein the first flow channel is curved in an arc shape, and one flow channel wall of the first flow channel has a curvature larger than a curvature of an other flow channel wall facing the one flow channel wall.

7. The flow channel structure according to claim 1, further comprising a structure that filters the foreign substance, the structure being provided on the first region.

8. The flow channel structure according to claim 7, wherein the structure that filters the foreign substance has a plurality of elongated protrusions arranged at intervals in parallel with each other along a flow direction in the first flow channel.

9. The flow channel structure according to claim 7, wherein the structure that filters the foreign substance has a plurality of columnar protrusions extending in a depth direction of the first flow channel.

10. The flow channel structure according to claim 1, wherein the first flow channel has a plurality of the first region.

11. The flow channel structure according to claim 1, wherein a depth and a width of the another region of the first flow channel are 0.1 mm to 3 mm.

12. The flow channel structure according to claim 1, further comprising:

a branching and rejoining channel downstream of the fourth flow channel, wherein the branching and rejoining channel has a branching portion which splits an upstream flow channel into two branched flow channels, and a rejoining portion which connects said two branched flow channels downstream of each other, and wherein one of the two branched flow channels has an area shallower in depth than the fourth flow channel at a downstream end, and the other of the two branched flow channels has an area shallower in depth than the fourth flow channel at a position other than the downstream end.

13. A method using the flow channel structure according to claim 1 to remove the foreign substance in a fluid, the method comprising flowing the fluid to the first flow channel.

14. A method for manufacturing lipid particles encapsulating drugs, comprising:

flowing each of a first solution containing lipids as a material of the lipid particles in an organic solvent and a second solution containing drugs in an aqueous solvent to the first flow channel of the flow channel structure according to claim 1, and removing a foreign substance in each of the first solution and the second solution;

mixing the first solution and the second solution after the removing of the foreign substance to obtain a mixed solution; and granulating the lipids by lowering a concentration of the organic solvent in the mixed solution to form the lipid particles encapsulating the drugs.

15. The method according to claim 14, wherein the mixing of the first solution and the second solution is performed using the two-liquid mixing flow channel, wherein the first solution from which the foreign substance is removed flows to one flow channel of the second flow channel and the third flow channel, and the second solution from which the foreign substance is removed flows to an other flow channel of the second flow channel and the third flow channel.

16. The method according to claim 14, further comprising, after the granulating, condensing a lipid particle solution containing the lipid particles.

* * * * *